(12) United States Patent
DeGrave et al.

(10) Patent No.: US 10,842,685 B2
(45) Date of Patent: Nov. 24, 2020

(54) METHOD OF MANUFACTURING BRIDGED ABSORBENT STRUCTURES

(71) Applicant: KIMBERLY-CLARK WORLDWIDE, INC., Neenah, WI (US)

(72) Inventors: Greg Joseph DeGrave, Combined Locks, WI (US); Michael Barth Venturino, Appleton, WI (US); Michael John Niemeyer, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 16/782,481

(22) Filed: Feb. 5, 2020

(65) Prior Publication Data

US 2020/0170844 A1   Jun. 4, 2020

Related U.S. Application Data

(62) Division of application No. 15/542,245, filed as application No. PCT/US2016/013511 on Jan. 15, 2016, now Pat. No. 10,588,784.

(Continued)

(51) Int. Cl.
*A61F 13/00*   (2006.01)
*A61F 13/15*   (2006.01)
*A61F 13/532*  (2006.01)

(52) U.S. Cl.
CPC .. *A61F 13/15642* (2013.01); *A61F 13/15764* (2013.01); *A61F 13/532* (2013.01); *A61F 2013/15926* (2013.01)

(58) Field of Classification Search
None
See application file for complete search history.

(56) References Cited

U.S. PATENT DOCUMENTS 3,973,291 A   8/1976 Kolbach
4,041,203 A   8/1977 Brock et al.
(Continued)

FOREIGN PATENT DOCUMENTS

EP   0217032 A2   4/1987
EP   2508156 A1   10/2012
(Continued)

OTHER PUBLICATIONS

International Preliminary Report on Patentability for International Application No. PCT/US2016/013511, dated Mar. 17, 2017, 23 pages.
(Continued)

*Primary Examiner* — Linda L Gray
(74) *Attorney, Agent, or Firm* — Armstrong Teasdale LLP

(57) ABSTRACT

A method of manufacturing an absorbent web includes moving a foraminous member in a machine direction. The foraminous member has at least one masking plate with a partitioned area including at least one partition defining a plurality of segments. The method further includes drawing air through the foraminous member and depositing fibrous material onto the foraminous member to form an absorbent web. The absorbent web has a bridged area with a reduced basis weight corresponding to the partitioned area of the masking plate. The bridged area has vertical interfaces separating web segments and fibrous material at least partly bridging the vertical interfaces.

20 Claims, 16 Drawing Sheets

Related U.S. Application Data

(60) Provisional application No. 62/107,006, filed on Jan. 23, 2015.

(56) References Cited

U.S. PATENT DOCUMENTS

| | | |
|---|---|---|
| 4,360,021 A | 11/1982 | Stima |
| 4,663,220 A | 5/1987 | Wisneski et al. |
| 4,915,897 A | 4/1990 | Farrington et al. |
| 5,156,902 A | 10/1992 | Pieper et al. |
| 5,226,992 A | 7/1993 | Morman |
| 5,486,166 A | 1/1996 | Bishop et al. |
| 5,490,846 A | 2/1996 | Ellis et al. |
| 5,820,973 A | 10/1998 | Dodge, II et al. |
| 6,330,735 B1 | 12/2001 | Hahn et al. |
| 6,630,088 B1 | 10/2003 | Venturino et al. |
| 6,981,297 B2 | 1/2006 | Venturino et al. |
| 8,871,123 B2 | 10/2014 | De Carvalho et al. |
| 10,588,784 B2 * | 3/2020 | DeGrave ............... A61F 13/532 |
| 2005/0109442 A1 | 5/2005 | Neubauer et al. |
| 2006/0105075 A1 | 5/2006 | Otsubo |
| 2013/0139960 A1 | 6/2013 | Maruyama et al. |

FOREIGN PATENT DOCUMENTS

| | | |
|---|---|---|
| EP | 2769705 A1 | 8/2014 |
| WO | 2013187291 A1 | 12/2013 |

OTHER PUBLICATIONS

Supplementary European Search Report issued in European Application No. 16740529 dated Jul. 23, 2018.

* cited by examiner

Schematic x-ray of absorbent pad gray scale x-ray image of absorbent pad

Dry absorbent pad basis weight contour plot from x-ray analysis

METHOD OF MANUFACTURING BRIDGED ABSORBENT STRUCTURES

CROSS REFERENCE TO RELATED APPLICATIONS

This application is a divisional of U.S. patent application Ser. No. 15/542,245 filed on Jul. 7, 2017, and entitled METHOD OF MANUFACTURING BRIDGED ABSORBENT STRUCTURES, which claims priority to International Application PCT/US2016/013511, filed on Jan. 15, 2016, which claims priority to U.S. Provisional Application No. 62/107,006 filed on Jan. 23, 2015. Each of these applications are incorporated herein in their entirety.

BACKGROUND

The field of this disclosure relates generally to bridged absorbent structures and methods of manufacturing bridged absorbent structures for use in absorbent articles, such as training pants, diapers, incontinence products, disposable underwear, medical garments, feminine care articles, absorbent swim wear, and the like.

In one general practice of forming fibrous webs, such as laid fibrous webs, a fibrous sheet of cellulosic or other suitable absorbent material is fiberized in a conventional fiberizer, or other suitable shredding or comminuting device, to form discrete fibers. In addition, particles of superabsorbent material are often mixed with the fibers. The fibers and superabsorbent particles are then entrained in an air stream and directed to a suitable foraminous forming surface upon which the fibers and superabsorbent particles are deposited to form a continuous absorbent fibrous web or discrete absorbent structures.

The forming surfaces utilized in such systems are typically constructed with a wire or screen grid and employ a suitable pneumatic flow mechanism, such as vacuum suction apparatus, to define a differential pressure zone on the forming surface and impose a pressure differential thereon. The pressure difference usually results in airflow through the openings or perforations in the screen or grid of the forming surface. The use of vacuum suction to draw the air-entrained fiber stream onto the forming surface, and pass the airflow through the forming surface has been employed in high-speed commercial operations.

Various mechanisms have been used during the formation process to produce gradations in basis weight of the resultant fibrous web. For example, suitable forming surfaces have been constructed with depressions or pocket regions for the formation of desired high-basis-weights in the formed fibrous web. Where the pocket regions have been large and deep, it has been difficult to direct desired amounts of fiber material into the pocket regions. In other devices, blocking components have been positioned underneath the forming surfaces to partially block the airflow through the forming surfaces and, thus, inhibit airlaid fibers from being deposited above the blocked off sections.

Some devices form voids in the fibrous web through the thickness of the fibrous web, which can produce gradations in basis weight along the fibrous web. However, the voids formed in the fibrous web are free from any fibrous material and penetrate through the entire depth of the fibrous web. As a result, the voids can affect the structural integrity of the web and do not allow for additional gradations of basis weight. Further, the known methods for producing gradations in basis weight along the fibrous webs do not provide gradations in the basis weight through the low basis weight areas of the fibrous web.

Accordingly, it is desirable to provide more reliable and more efficient methods and apparatus for forming laid fibrous webs having gradations of basis weight. It is further desirable to provide easily assembled and modified apparatus for forming laid fibrous webs.

BRIEF DESCRIPTION

In one aspect, a method of manufacturing an absorbent web comprises moving a foraminous member in a machine direction. The foraminous member has at least one masking plate with a partitioned area including at least one partition defining a plurality of segments. The method further comprises drawing air through the foraminous member and depositing fibrous material onto the foraminous member to form an absorbent web. The absorbent web has a bridged area with a reduced basis weight corresponding to the partitioned area of the masking plate. The bridged area has vertical interfaces separating web segments and fibrous material at least partly bridging the vertical interfaces.

In another aspect, a method of forming an absorbent structure for use in an absorbent article comprises moving a forming surface having at least one masking plate mounted thereon in a machine direction. Air is drawn through the forming surface and the masking plate mounted on the forming surface. The masking plate has partitions that are less than 1 cm for at least partially blocking air being drawn through the forming surface. The method further comprises depositing fibrous material on the forming surface to form an absorbent web. The partitions of the masking plate displace the fibrous material into a plurality of segments separated by vertical interfaces. The vertical interfaces corresponding to the locations of the partitions. The absorbent web is removed from the forming surface.

In yet another aspect, a method of assembling an absorbent article including a bridged absorbent structure comprises forming a web of fibrous material. The web has a continuous area and a bridged area. The bridged area includes a plurality of segments separated by vertical interfaces. The continuous area has a higher basis weight than the bridged area. The web is divided into a first absorbent structure and a second absorbent structure. The first absorbent structure includes the continuous area and the bridged area. The method further comprises assembling a chassis having an outer cover and a body-side liner and securing the first absorbent structure between the outer cover and the body-side liner.

DETAILED DESCRIPTION OF THE DRAWINGS

Figure 1:
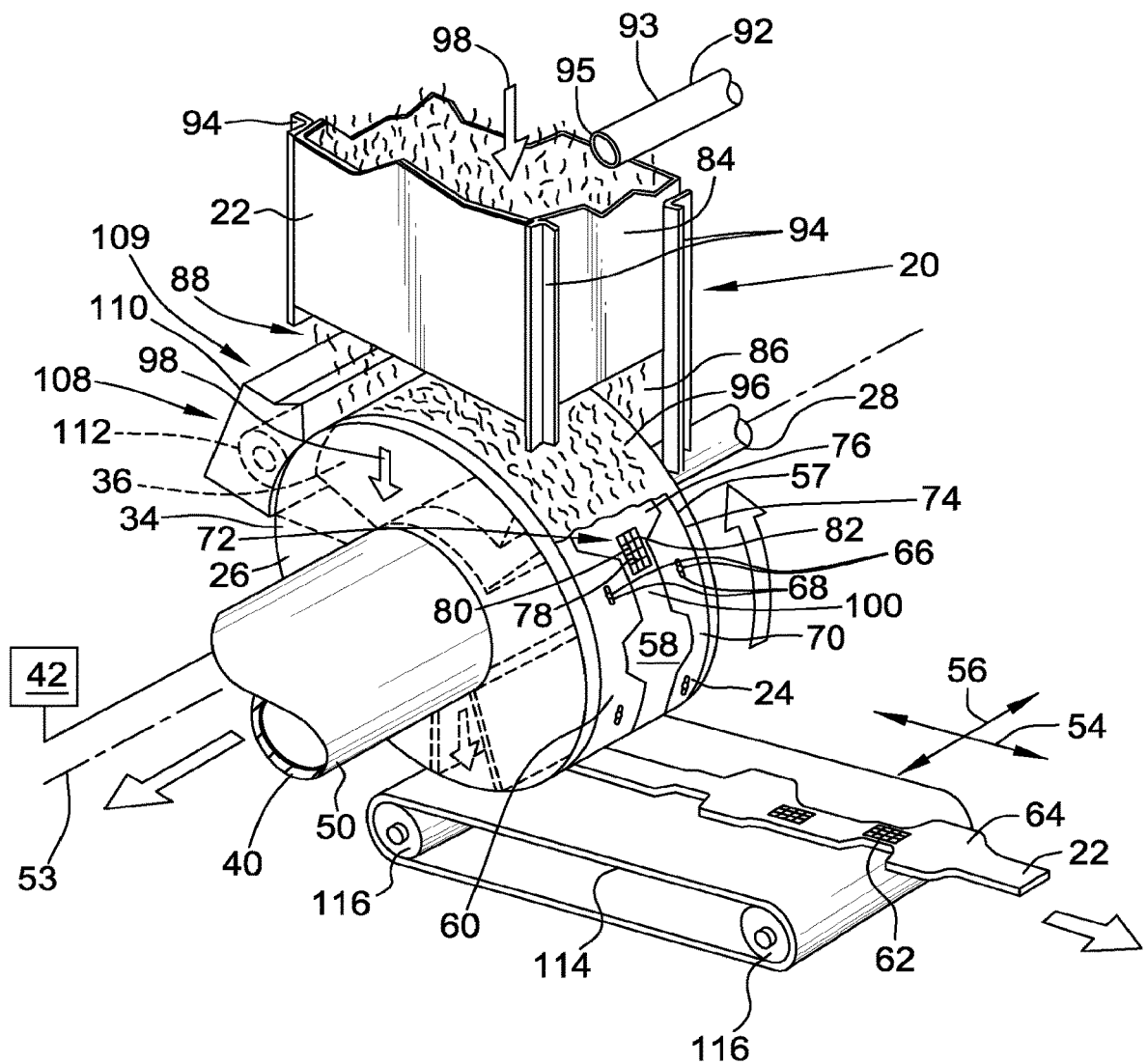
FIG. 1 is a perspective view of one suitable embodiment of a forming assembly for forming absorbent webs.
Figure 2:
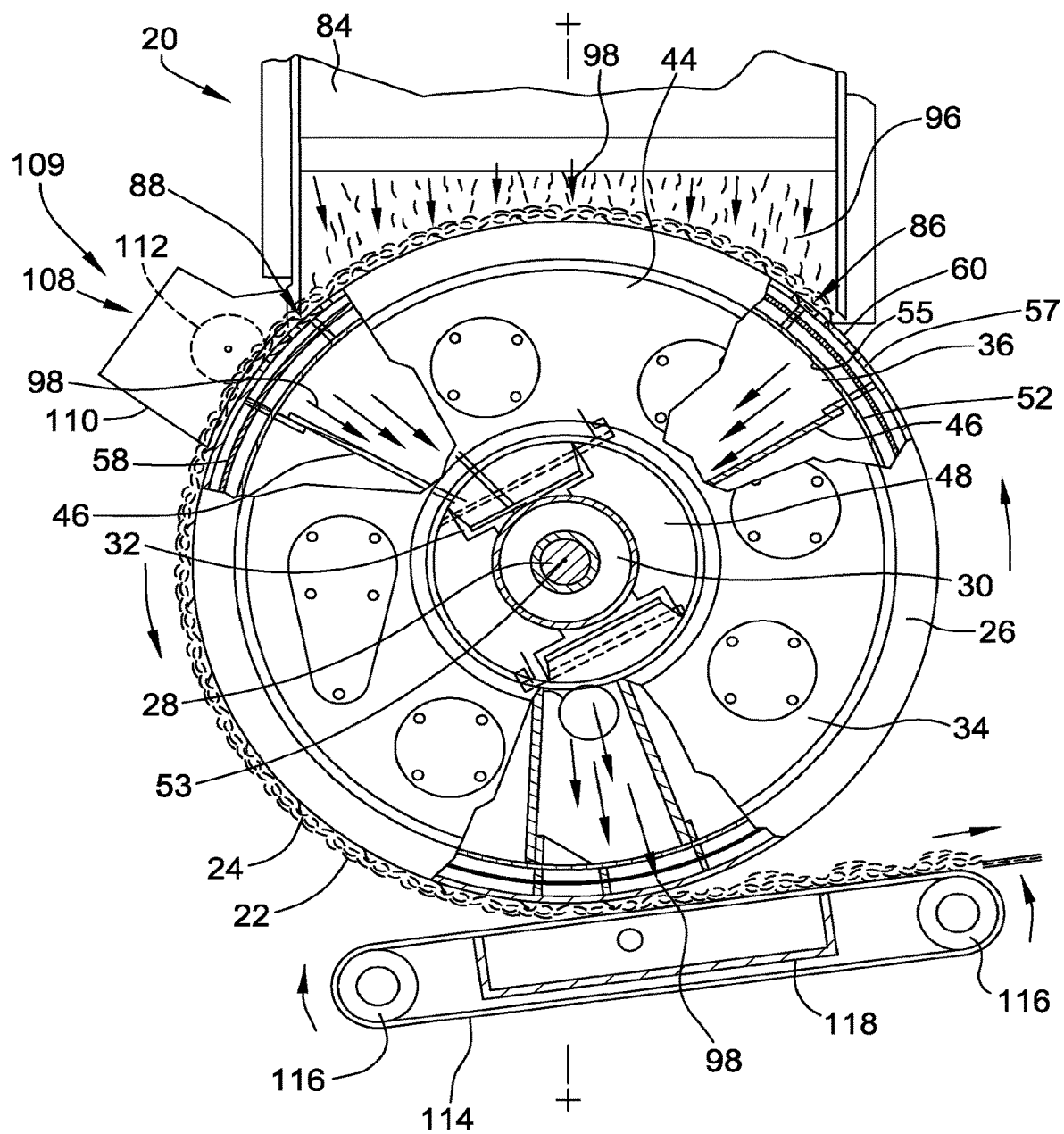
FIG. 2 is a side view of the forming assembly of FIG. 1 with portions removed to reveal inner parts.

With reference now to the drawings, and in particular to FIGS. 1 and 2, an apparatus for forming a fibrous web is illustrated and indicated generally by reference number 20. Apparatus 20 includes a movable, foraminous forming surface 24 extending around the circumference of a drum 26. The forming drum 26 is mounted on a shaft 28 connected by bearings 30 to a support 32. The forming drum 26 includes a circular drum wall (not shown) operatively connected to and rotated by the drum drive shaft 28. The shaft 28 is driven in rotation by a suitable motor or line shaft (not shown) in a counterclockwise direction as seen in FIG. 2. The drum wall can be a primary, load-bearing member, and the drum wall can extend generally radially and circumferentially about the drum drive shaft 28.

A vacuum duct 36 located radially inwardly of the forming surface 24 extends over an arc of the interior of the forming drum 26. The vacuum duct 36 is in fluid communication with the forming surface 24 for drawing air through the forming surface 24. The vacuum duct 36 is mounted on and in fluid communication with a vacuum supply conduit 40 connected to a vacuum source 42. The vacuum source 42 may be, for example, an exhaust fan. The vacuum duct 36 is connected to the vacuum supply conduit 40 along an outer peripheral surface of the vacuum supply conduit 40, and extends circumferentially of the vacuum supply conduit 40. The vacuum duct 36 projects radially outwardly from the vacuum supply conduit 40 toward the forming surface 24 and includes axially spaced side walls 44 and angularly spaced end walls 46.

The shaft 28 extends through the drum wall and into the vacuum supply conduit 40 where it is received in the bearing 30 connected to the support 32 within the vacuum supply conduit 40. The bearing 30 is sealed with the vacuum supply conduit 40 so that air is not drawn in around the shaft 28 where it enters the vacuum supply conduit 40.

As representatively shown, the vacuum supply conduit 40 can include a conduit end wall 48 and a peripheral wall 50 that delimit the size and shape of the vacuum supply conduit 40. The vacuum supply conduit 40 can have any suitable cross-sectional shape. In the illustrated configuration, the vacuum supply conduit 40 has a generally circular cross-sectional shape. The vacuum supply conduit 40 can be operatively held in position with any suitable support structure. The support structure can also be joined and connected to further components or members that operatively support the portions of the vacuum supply conduit 40 structure that engage the drum drive shaft 28, such as the support 32. For example, in the exemplary embodiment, the support 32 and the entire vacuum supply conduit 40 are supported by an overhead mount (not shown).

In the illustrated embodiment, walls 34 extend generally radially and circumferentially about the vacuum supply conduit 40. A drum rim 52 is joined to the walls 34, and is constructed and arranged to provide a substantially free movement of air through the thickness of the drum rim 52. The drum rim 52 is generally cylindrical in shape and extends along the direction of the drum axis 53, and circumferentially about the drum axis 53. As representatively shown, the drum rim 52 can be supported by and extend between the walls 34. The drum rim 52 has an inward-facing surface 55 that faces the vacuum duct 36.

With reference to FIGS. 1 and 2, the forming surface 24 can be provided along the outer, cylindrical surface of the forming drum 26, and can extend along the axial and circumferential dimensions of the forming drum. The circumferential dimension is generally in a machine direction 54 and the axial dimension is generally in a cross-machine direction 56. The structure of the forming surface 24 can be composed of an assembly, and can include a foraminous member 58, which is operatively connected and joined to the forming drum 26. In the illustrated embodiment, a system of inserts 57 forms the forming surface 24 and the foraminous member 58.

The forming surface 24 can be operatively held and mounted on the drum rim 52 by employing any suitable attachment mechanism. As representatively shown, a system of nuts and bolts can be employed to secure the inserts 57 onto an operative set of mounting rings, and the mounting rings can be operatively mounted on and secured to the drum rim 52.

Suitable forming drum systems for producing airlaid fibrous webs are well known in the art. For example, see U.S. Pat. No. 4,666,647 entitled APPARATUS AND METHOD FOR FORMING A LAID FIBROUS WEB by K. Enloe et al. which issued May 19, 1987; and U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference in a manner that is consistent herewith. Other forming drum systems are described in U.S. Pat. No. 6,330,735, entitled APPARATUS AND PROCESS FOR FORMING A LAID FIBROUS WEB WITH ENHANCED BASIS WEIGHT CAPABILITY by J. T. Hahn et al. which issued Dec. 18, 2001, the entire disclosure of which is incorporated herein by reference in a manner that is consistent herewith. Systems for forming surfaces are described in U.S. Pat. No. 6,363,088, entitled FORMING MEDIA WITH ENHANCED AIR FLOW PROPERTIES by Michael Barth Venturino et al. which issued Oct. 7, 2003, the entire disclosure of which is incorporated herein by reference in a manner that is consistent herewith.

In other embodiments, the apparatus 20 may have any type of forming surface 24. For example, the forming surface 24 may be provided by an endless forming belt. Forming belt systems for producing fibrous webs are well known in the art. Examples of such forming belt systems are available from the Paper Converting Machine Company, a business having offices located in Green Bay, Wis., U.S.A.; and from Curt G. Joa Incorporated, a business having offices located in Sheboygan Falls, Wis., U.S.A.

At least one masking plate 60 can be disposed on the foraminous member 58. Preferably, a cooperating system of masking plates 60 are disposed on the foraminous member 58 and configured to extend circumferentially around the forming drum 26. The masking plates 60 facilitate forming gradations in basis weight through the fibrous web 22, as will be described in more detail below. Preferably, the masking plates 60 are configured to form bridged areas 62 of lower basis weight relative to continuous areas 64 of higher basis weight in the fibrous web 22. As used herein, basis weight means the amount of fibrous material per unit of area and is used to compare the relative amount of fibrous material in different areas of a web.

In suitable embodiments, the system of masking plates 60 can include masking plates 60 that have any number of different patterns and are arranged in any order. The illustrated system of masking plates 60 includes substantially identical masking plates 60 arranged consecutively around the circumference of the forming drum 26. As representatively shown, the masking plates 60 can be joined and assembled to the forming surface 24 by employing conventional attaching or mounting mechanisms. In the exemplary embodiment, the masking plates 60 are secured to the forming surface 24 by a plurality of bolts 66 inserted through holes 68 in the masking plates 60 and the forming surface 24.

The masking plates 60 are positioned on the radially outer surface of the forming surface 24 on the forming drum 26, which facilitates easy replacement and/or repositioning of the masking plates 60. The masking plates 60 are relatively inexpensive to produce and easy to install.

The masking plates 60 may have any shape suitable for mounting on the inserts 27. In the illustrated embodiment, for example, the masking plates 60 have an outer perimeter that forms a substantially rectangular shape. Additionally, the masking plates 60 have a slight curve along their length in the machine direction 54 to form an arc for fitting on the cylindrical forming surface 24, as can be seen best in FIG. 12. In other suitable embodiments, the masking plates 60 may be substantially flat for fitting on planar forming surfaces (not shown). The curve of each masking plate 60 has a radius substantially equal to the radius of the forming surface 24 such that the masking plates 60 fit on the forming surface 24. When joined together, a series of masking plates 60 can completely encircle the circumference of the forming surface 24.

The apparatus 20 further includes a forming chamber 84 through which the forming surface 24 is movable. The forming chamber 84 has an entrance 86 where the forming surface 24 enters the chamber substantially free of fibrous material and an exit 88 where the forming surface 24 leaves the chamber substantially filled with fibrous material. A fiberizer (not shown) provides fibrous material into the forming chamber 84, and the vacuum source 42 creates a vacuum pressure in the vacuum duct 36 relative to the interior of the forming chamber 84. As the forming surface 24 enters and then traverses through the forming chamber 84, the component materials of the fibrous web 22 are operatively carried or transported by an entraining air stream that is drawn through the forming surface 24. The pressure differential across the forming surface 24 causes the fluent fibers in the forming chamber 84 to be drawn to the forming surface 24.

The selected fibrous material may be suitably derived from a batt of cellulosic fibers (e.g., wood pulp fibers) or other source of natural and/or synthetic fibers, which has been disintegrated, in a manner well known in the art, to provide an operative quantity of individual, loose fibers. Accordingly, the fiberizer (not shown) can operatively receive a selected web-forming material, convert the web-forming material into individual fibers, and deliver the fibers into the forming chamber 84. The fiberizer can be a rotary hammer mill, a rotatable picker roll, or any other suitable fiberizer. In some embodiments, the fibers can be chemically altered or curled fibers.

Other component materials for producing the fibrous web 22 may also be delivered into the forming chamber 84. For example, particles or fibers of superabsorbent material may be introduced into the forming chamber 84 by employing conventional mechanisms, such as pipes, channels, spreaders, nozzles and the like, as well as combinations thereof. In the representatively shown configuration, the superabsorbent material can be delivered into the forming chamber 84 by employing a delivery system 92, such as the illustrated operative conduit and nozzle system. The illustrated operative conduit and nozzle system includes a conduit 93 and a nozzle 95. The illustrated orientation of the delivery conduit 93 is exemplary, and it should be readily appreciated that any operative orientation of the delivery conduit 93 and nozzle 95 may be employed. The fibers, particles and other desired web material may be entrained in any suitable gaseous medium. Accordingly, any references herein to air as being the entraining medium should be understood to be a general reference which encompasses any other operative entrainment gas. Superabsorbent materials are well known in the art, and are readily available from various suppliers. For example, FAVOR 880 superabsorbent is available from Stockhausen, Inc., a business having offices located in Greensboro, N.C., U.S.A.; and BASF 9700 is available from BASF Corporation, a business having offices located in Charlotte, N.C., U.S.A.

Examples of techniques that can be used to introduce superabsorbent particles into the forming chamber 84 are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990; the entire disclosure of which is incorporated herein by reference in a manner that is consistent herewith.

The particles or fibers of superabsorbent material may be introduced into the forming chamber 84 and deposited on the forming surface 24 such that the fibrous web 22 is formed with a desired percentage of superabsorbent material. Preferably, the fibrous web 22 may include between about 0% and 90% superabsorbent material. Even more preferably, the fibrous web 22 may include between about 50% and 80% superabsorbent material.

In suitable embodiments, the fibrous web 22 may have different amounts of superabsorbent material in different locations. For example, higher basis weight areas of the fibrous web 22 may have higher concentrations of superabsorbent material and lower basis weight areas may have lower concentrations of superabsorbent material. In other suitable embodiments, the superabsorbent material may be distributed uniformly throughout the fibrous web 22.

The stream of air-entrained fibers and particles can pass through the forming chamber 84 for deposition onto the selected forming surface 24. The forming chamber 84 can serve to direct and concentrate the air-entrained fibers and particles, and to provide a desired velocity profile in the air-entrained stream of fibers and particles. Typically, the forming chamber 84 is supported by suitable structural members 94, which together form a support frame for the forming chamber 84. The frame may be anchored and/or joined to other suitable structural components, as necessary or desirable.

The portion of the forming drum 26 which, at a particular point in time, is positioned within the boundaries of the forming chamber 84 can delimit or otherwise provide a vacuum lay-down zone 96 of the forming surface 24. As representatively shown, the vacuum lay-down zone 96 can constitute a circumferential, cylindrical surface portion of the rotatable drum 26. An operative pressure differential is imposed on the surface of the vacuum lay-down zone 96 under the action of the vacuum source 42. The vacuum source 42 can be any conventional vacuum generating mechanism, such as a vacuum pump, an exhaust blower or other suitable mechanism which can provide a relatively lower pressure under the forming surface 24. The vacuum source 42 can operatively withdraw air from the arcuate segment of the forming drum 26 associated with the vacuum lay-down surface 96 through the vacuum duct 36 and the vacuum supply conduit 40. Accordingly, air flows through the forming chamber 84 and the forming drum 26 in the direction of arrows 98.

In a representative operation, the airlaid fibrous web 22 can be formed from the stream of air-entrained fibers (and particles) as the entrainment gas flows through the openings in the forming surface 24 and into the rotating forming drum 26. Under the influence of the vacuum source 42, a conveying air stream is drawn through the forming surface 24 into the interior of the forming drum 26, and is subsequently passed out of the forming drum 26 through the vacuum supply conduit 40. As the air-entrained fibers and particles impinge on the forming surface 24, the air component is passed through the forming surface 24 and the fibers-particles component is retained on the forming surface 24 to form the nonwoven fibrous web 22 thereon. In suitable embodiments, a substrate 144 (shown in FIG. 4) can be positioned on the forming surface 24 to receive the deposited fibers-particles component. The substrate 144 is at least partly air-permeable so the entrainment gas can flow through the substrate and through the forming surface 24. In suitable embodiments, the substrate 144 can be a nonwoven material.

In suitable embodiments, at least a portion of each masking plate 60 blocks or otherwise occludes the flow of air through selected regions of the forming surface 24. As a result, the masking plates 60 can deflect or reduce the amount of fibers deposited on the areas of the forming surface 24 that are covered by the masking plates 60, i.e., the masking plates 60 at least partly displace the fibrous material.

The exemplary masking plates 60 have side walls 70 and partitions 72 extending between the side walls 70 to displace the fibrous material (FIG. 1). The side walls 70 have outboard side edges 74 and inboard side edges 76. In desired arrangements, the inboard side edges 76 of the masking plates 60 can be contoured. In the representatively shown arrangement, the side walls 70 of the masking plates 60 have a serpentine, undulating contour defined by the inboard side edges 76 along the machine direction 54. Additionally, the masking plates 60 can be cooperatively arranged and configured to provide alternating, narrow and wide regions over the forming surface 24 that allow air flow through the forming surface 24. In some embodiments, the masking plates 60 can be symmetric such that the contours of the inboard side edges 76 can be substantially mirror images of each other. The inboard side edges 76 of the masking plates 60 can optionally have a substantially straight configuration along the machine-direction 54 to expose a substantially rectangular, ribbon shaped region of the foraminous member 58.

The partitions 72 at least partially block air flow through the forming surface 24 between the side walls 70 of the masking plate 60. It is understood the masking plate 60 can include any number of partitions 72 extending in any directions. In the illustrated embodiment, the partitions 72 include lateral partitions 78 and longitudinal partitions 80. The lateral partitions 78 extend at least partially in the cross-machine direction 56. The longitudinal partitions 80 extend at least partially in the machine direction 54. In the illustrated embodiment, at least some of the lateral and longitudinal partitions 78, 80 are substantially perpendicular.

Additionally, the partitions 72 may have any shapes and combinations of shapes, e.g., without limitation, curved and/or straight shapes. Moreover, the partitions 72 may have any size. Preferably, each partition 72 has a width that is less than 1 cm and, even more preferably, has a width that is less than ½ cm. The width of the partition facilitates directing the fibrous material, as will be discussed in more detail below.

In the exemplary embodiment, the masking plates 60 include at least one open area 100. The open area 100 is substantially free of obstructions to the deposition of web material on the forming surface 24. Preferably, the open area 100 has a continuous area between about 10 $cm^2$ and about 750 $cm^2$. More preferably, the open area 100 has a continuous area between about 200 $cm^2$ and about 500 $cm^2$.

The partitions 72 substantially block airflow through a portion of the forming surface 24 and, therefore, inhibit the deposition of fibrous material on the forming surface 24. The partitions 72 also displace fibrous material due to the pattern height 131 of the masking plate 60, which will be described in more detail below. The areas between the partitions 72 form segments 102 through which the fibrous material can be directed onto the forming surface 24. Preferably, each segment 102 has an area between about 10 $mm^2$ and about 2,500 $mm^2$. More preferably, each segment 102 has an area between about 25 $mm^2$ and about 2,000 $mm^2$. Even more preferably, each segment 102 has an area between about 100 $mm^2$ and about 1,000 $mm^2$.

Together the partitions 72 and the segments 102 define the partitioned areas 82. Preferably, the partitions 72 cover between about 20% and about 75% of the partitioned area 82. More preferably, the partitions 72 cover between about 20% and about 40% of the partitioned area 82. The partitions 72 at least partially inhibit deposition of fibrous material in the partitioned areas 82 and, therefore, displace the fibrous material to the open areas 100. As a result, the partitioned areas 82 will form portions of the fibrous web 22 that have lower basis weights than the portions of the fibrous web 22 formed by the open areas 100.

Suitably, the masking plates 60 can be used to form fibrous webs 22 having a basis weight profile through the fibrous web 22. Preferably the fibrous web 22 has a ratio of higher basis weight area to lower basis weight area of at least 1.25:1. More preferably, the fibrous web 22 has a ratio of higher basis weight area to lower basis weight area of at least 1.33:1. Even more preferably, the fibrous web 22 has a ratio of higher basis weight area to lower basis weight area of at least 1.5:1.

The bridged areas 62 can be formed in the fibrous web 22 corresponding to the locations of the partitioned areas 82. Additionally, the continuous areas 64 can be formed in the fibrous web 22 corresponding to the locations of the open areas 100. The bridged areas 62 generally have lower basis weights than the continuous areas 64. Therefore, the fibrous web 22 has a gradation of basis weight through the fibrous web 22 due to the variations between the lower basis weight bridged areas 62 and the higher basis weight continuous areas 64.

Figure 6:
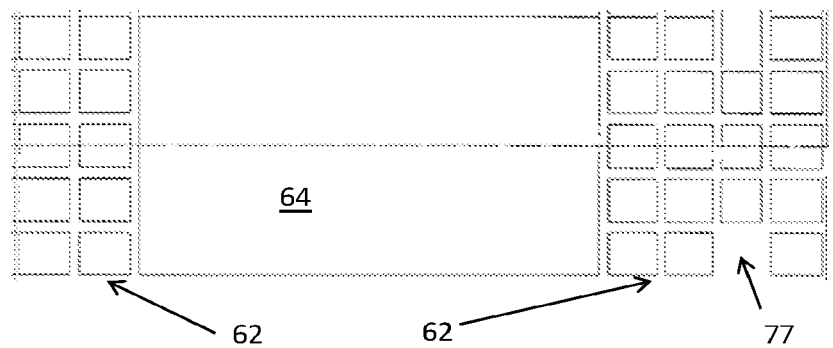
FIG. 6 is a series of x-ray views of an absorbent structure showing gradations of basis weight through the absorbent structure.
Figure 6:
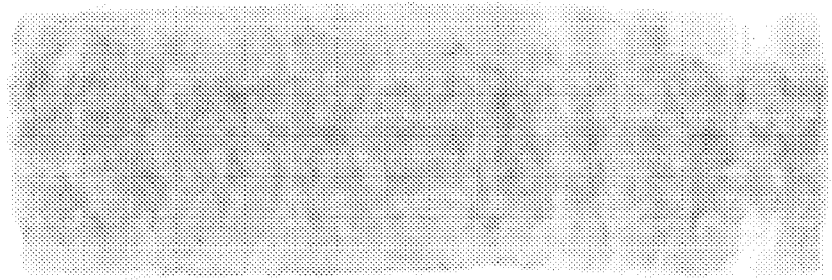
Figure 6:
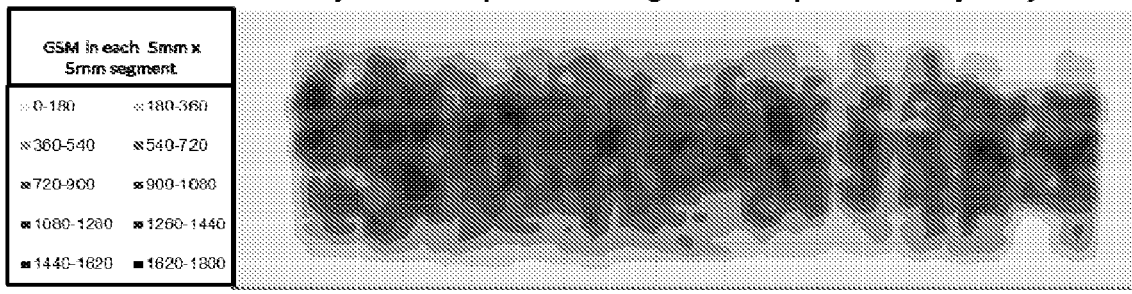

The masking plates 60 can optionally be configured to form other desired elements, such as a series of key notches or other through-holes, on the laid fibrous web 22. One example of an absorbent structure having a key notch 77 is shown in FIG. 6. The key notches 77 can, for example, provide sensing points for locating and positioning a subsequent severing of the longitudinally extending fibrous web 22 into discrete fibrous pads. In suitable embodiments, the key notches 77 are formed by substantially inhibiting the deposition of fibrous material over a width large enough to prevent bridging and create a void through the thickness of the pad.

As illustrated, the masking plates 60 facilitate forming fibrous webs having gradations in basis weight on the forming surface 24 that has a substantially uniform depth along its surface, i.e., is a flat forming surface. However, in suitable embodiments, the forming surface 24 and, particularly, the foraminous member 58 can include a forming surface contour which is non-uniform along its depth dimension. For example, the foraminous member 58 can include a plurality of longitudinally spaced-apart pocket regions (not shown) for forming high-basis weight regions. Cooperating non-pocket regions of the foraminous member 58 can be interposed between the pocket regions, and can be appointed for the formation of low-basis-weight regions of the fibrous web 22.

After formation of the airlaid fibrous web 22, the drum rotation can then pass the fibrous web 22 from the vacuum lay-down zone 96 to a scarfing zone 109 where excess thickness of the fibrous web 22 can be trimmed and removed to a predetermined extent by a scarfing system 108. The scarfing system 108 may be positioned at the exit region 88 of the forming chamber 84. The scarfing system 108 can include a scarfing chamber 110 and a scarfing roll 112, which is positioned within the scarfing chamber 110. The scarfing roll 112 can abrade excess fibrous material from the fibrous web 22, and the removed fibers can be transported away from the scarfing chamber 110 with a suitable discharge conduit, as is well known in the art. The removed fibrous material may, for example, be recycled back into the forming chamber 84 or the fiberizer, as desired. Additionally, the scarfing roll 112 can rearrange and redistribute the web material along the longitudinal machine direction 54 of the web and/or along the lateral cross-machine direction 56 of the fibrous web 22.

Additional redistribution during the scarfing process to create areas of higher basis weight in the fibrous web 22 is unnecessary because the masking plates 60 displace the fibrous material to form areas of higher basis weight during the formation of the fibrous web 22. However, in some suitable embodiments, the scarfing system 108 may be used to redistribute the fibrous material to further delineate the gradation in basis weight.

The rotatable scarfing roll 112 is operatively connected and joined to a suitable shaft member, and is driven by a suitable drive system (not shown). The drive system may include any conventional apparatus, such as a motor or a coupling to the drive mechanism employed to rotate the forming drum 26. The scarfing system 108 can provide a conventional trimming mechanism for removing or redistributing any excess thickness of the laid fibrous web 22 that has been deposited on the forming surface 24. The surface of the scarfing roll 112 can be adjusted to provide a desired contour along the scarfed surface of the fibrous web 22. In the representatively shown arrangement, the scarfing roll 112 can, for example, be configured to provide a substantially flat surface along the scarfed surface of the fibrous web 22. The scarfing roll 112 can optionally be configured to provide a non-flat surface. The scarfing roll 112 is disposed in closely spaced relationship to the forming surface 24, and the forming surface 24 is translated past the scarfing roll 112. A conventional transporting mechanism, such as a suction fan (not shown) can draw the removed fibrous material away from the formed fibrous web 22 and out from the scarfing chamber 110.

In the representatively shown configuration, the scarfing roll 112 rotates in a direction which moves a contacting surface of the scarfing roll 112 in a counter-direction that is opposite the movement direction of the laid fibrous web 22. Alternatively, the scarfing roll 112 may be rotated to provide a co-directional movement of the roller surface relative to the surface of the forming drum 26 most proximate thereto. In either situation, the rotational speed of the scarfing roll 112 should be suitably selected to provide an effective scarfing action against the contacted surface of the formed fibrous web 22. Any other suitable trimming mechanism may be employed in place of the scarfing roll assembly to provide a cutting or abrading action to the laid fibrous web 22 by a relative movement between the fibrous web 22 and the selected trimming mechanism.

After the scarfing operation, the formed fibrous web 22 can be removed from the forming surface 24. The removal operation may be provided by the weight of the fibrous web 22, by centrifugal force, and/or by a positive air pressure. With the rotation of the forming drum 26, the portion of the forming surface 24 that is carrying the airlaid fibrous web 22 can be moved to an optional pressure blow-off zone of the forming drum 26. In the blow-off zone, air can be introduced under pressure and directed radially outwardly against the fibrous web 22 on the portion of the forming surface 24 that becomes aligned with the blow-off zone. The gas pressure can affect a ready release of the fibrous web 22 from the forming surface 24, and the fibrous web 22 can be removed from the forming surface 24 onto a suitable transport mechanism. In suitable embodiments, the substrate 144 can be used to support the fibrous web 22 and facilitate removing the fibrous web 22 from the forming surface 24.

A web transporter can receive the formed fibrous web 22 from the forming drum 26, and convey the fibrous web 22 for further processing. Suitable web transporters can, for example, include conveyer belts, vacuum drums, transport rollers, electromagnetic suspension conveyors, fluid suspension conveyors or the like, as well as combinations thereof. As representatively shown, the web transporter can be provided by a system which includes an endless conveyor belt 114 disposed about rollers 116.

In a particular configuration of the invention, a vacuum box 118 can be located below the conveyor belt 114 to help remove the fibrous web 22 from the forming surface 24. The vacuum box 118 opens onto the belt 114, and a suction of air out of the vacuum box 118 can draw an air flow through perforations in the conveyor belt 114. This flow of air can, in turn, operate to draw the fibrous web 22 away from the forming surface 24. The vacuum box 118 can be employed with or without the use of a positive pressure in the blow-off zone. The removed fibrous web 22 can provide an interconnected series of pads, and each pad can have a selected surface contour which substantially matches the contour provided by the various, corresponding portions of the forming surface 24 and masking plates 60 upon which each individual pad was formed.

Figure 3:
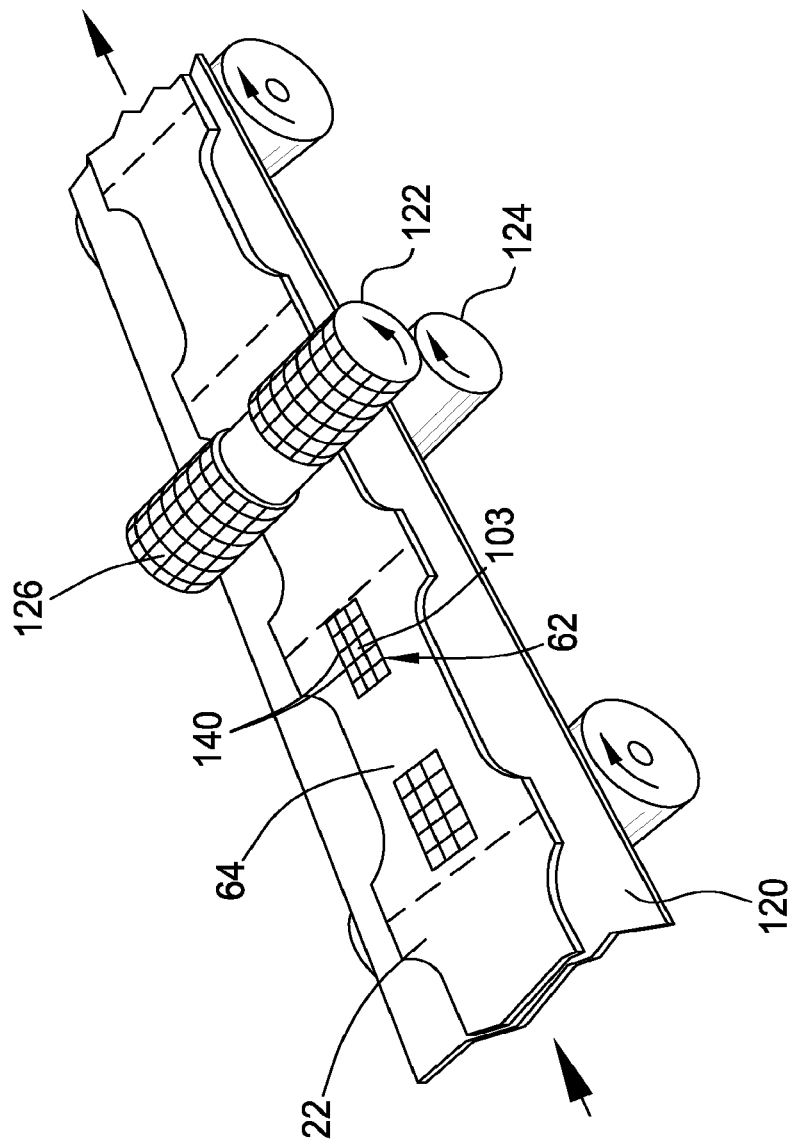
FIG. 3 is a perspective view of a portion of a debulking line for use with the forming assembly of FIGS. 1 and 2.

As is illustrated in FIG. 3, the fibrous web 22 after leaving the forming drum 26 is passed onto a belt 120 where debulking compression rolls 122 and 124 compress the material to provide it with more strength and to debulk it for easier handling. It is believed that debulking enhances fiber entanglement so that a stronger interconnection of the fibrous material may be achieved. In the illustrated embodiment, the roll 122 has a pattern of protrusions 126 that imprint a pattern on at least one surface of the fibrous web 22. The protrusions 126 are relatively small deviations from the surface level of the roll generally being only about 1.27 cm. In other embodiments, the rolls 122 and 124 may be any type of debulking rolls, e.g., without limitations rolls having indentations and/or cavities. In some embodiments, the debulking rolls may be smooth and may not impart a pattern to the fibrous web 22.

The debulking rolls 122, 124 desirably define a nip which is smaller than the thickness of the fibrous web 22. In one suitable embodiment, the distance between the rolls 122 and 124 is about 0.38 mm in the protrusion areas and about 1.65 mm in the level areas of the rolls. Thus, the fibrous web 22 is compressed and markedly reduced in thickness by operation of the debulking rolls 122, 124. The fibers of the fibrous web 22 undergo considerable deformation when passing through the nip of the rolls 122, 124, especially at high speeds and significant compression. As a result, the debulking process facilitates additional displacement of fibrous material from the web segments 103 into the vertical interfaces 140, which creates additional bridging 142 and pronounces the micro-gradient of basis weight. In some suitable embodiments, the debulking process can be omitted.

It will be readily apparent that various conventional devices and techniques can be employed to further process the fibrous web 22. For example, various conventional devices and techniques (not shown) can be employed to sever the fibrous web 22 into predetermined lengths to provide selected air formed fibrous pads, e.g., absorbent structures. The severing system may, for example, include a die cutter, a water cutter, rotary knives, reciprocating knives, energy beam cutters, particle beam cutters or the like, as well as combinations thereof. After severing, the discrete fibrous pads can be transported and delivered for further processing operations, as desired.

Suitable systems for forming and processing the fibrous pads are well known in the art. For example, see U.S. Pat. App. Pub. No. 2007/0049892 entitled ABSORBENT ARTICLE WITH CORE WRAP by Patrick Lord et al. published Mar. 1, 2007; and U.S. Pat. App. Pub. No. 2007/0044903 entitled METHOD AND APPARATUS FOR MAKING ABSORBENT ARTICLE WITH CORE WRAP by Anthony Wisneski et al. published Mar. 1, 2007; the entire disclosures of which are incorporated herein by reference in a manner that is consistent herewith.

In suitable embodiments, the fibrous web 22 and/or fibrous pads can be folded. For example, the longitudinal or transverse edges of the fibrous web 22 can be folded prior to severing. In suitable embodiments, the fibrous web 22 and/or fibrous pads can be folded about a fold line such that at least part of the bridged area 62 is folded. In some embodiments, the fold line substantially coincides with at least one of the vertical interfaces 140. The fibrous web 22 and fibrous pads may be folded by any known folding system, for example, vacuum systems and systems including mechanical folding structures such as folding skis, folding boards, and folding bars.

Figure 15:
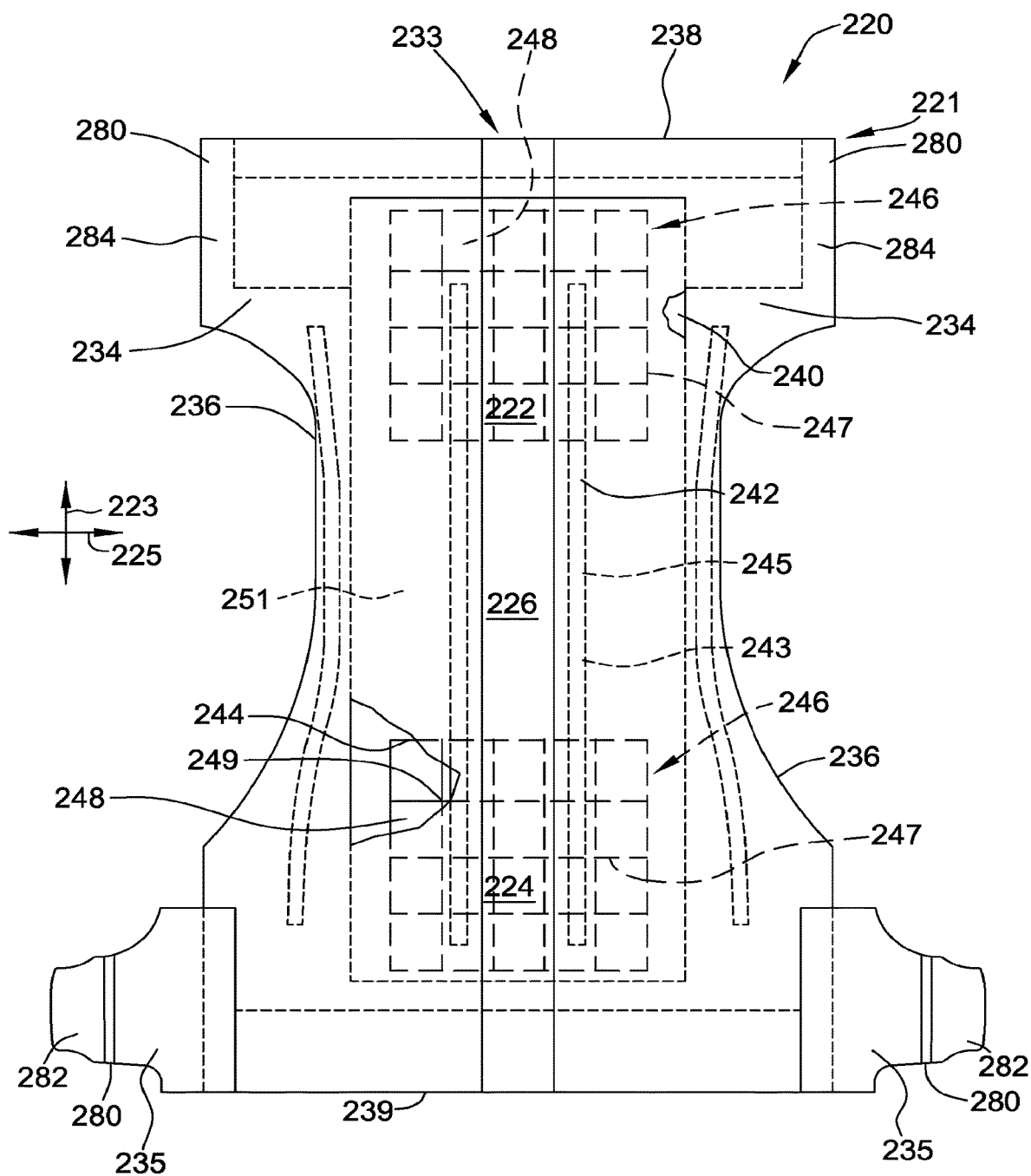
FIG. 15 is top plan view of an absorbent article incorporating one suitable embodiment of a bridged absorbent structure, the absorbent article being illustrated in a laid flat configuration.

In some embodiments, at least one face of the fibrous pads may be covered by a wrapsheet 251 (shown in FIG. 15). The wrapsheet 251 can be wrapped around the fibrous pads such that the wrapsheet 251 covers the side edges and portions of the opposed faces of the fibrous pads. The wrapsheet 251 can be secured to the fibrous pads to prevent unwrapping. Examples of techniques that can be used to fold and wrap fibrous pads are described in U.S. Pat. No. 7,396,349 entitled WRAPPED ABSORBENT CORE by James George Van Himbergen et al., which issued Jul. 8, 2008; the entire disclosure of which is incorporated herein by reference in a manner that is consistent herewith.

The masking plates 60 facilitate producing absorbent structures that are shaped and have gradations in basis weight designed for absorbent articles. Accordingly, the masking plates 60 can be used in apparatus for making absorbent structures for use in disposable absorbent articles, such as diapers, children's training pants, feminine care products, adult incontinence products and the like.

Preferably, the fibrous web 22 is divided such that each formed absorbent structure has at least one bridged area 62 that covers between about 20% and about 75% of the entire area of the absorbent structure. More preferably, the bridged area 62 for each formed absorbent structure covers between about 30% and about 66% of the entire area of the absorbent structure. Most preferably, the bridged area 62 for each formed absorbent structure covers between about 33% and about 60% of the entire area of the absorbent structure. In some embodiments, the area of the bridged areas 62 may vary depending on the intended use of the absorbent structure. For example, if the absorbent structure is to be used in a gender specific personal care article, the bridged area 62 preferably covers approximately 53% of the entire area of the absorbent structure. If the absorbent structure is intended for non-gender specific personal care items, such as diapers, the bridged area 62 preferably covers approximately 42% of the entire area of the absorbent structure.

Figure 4:
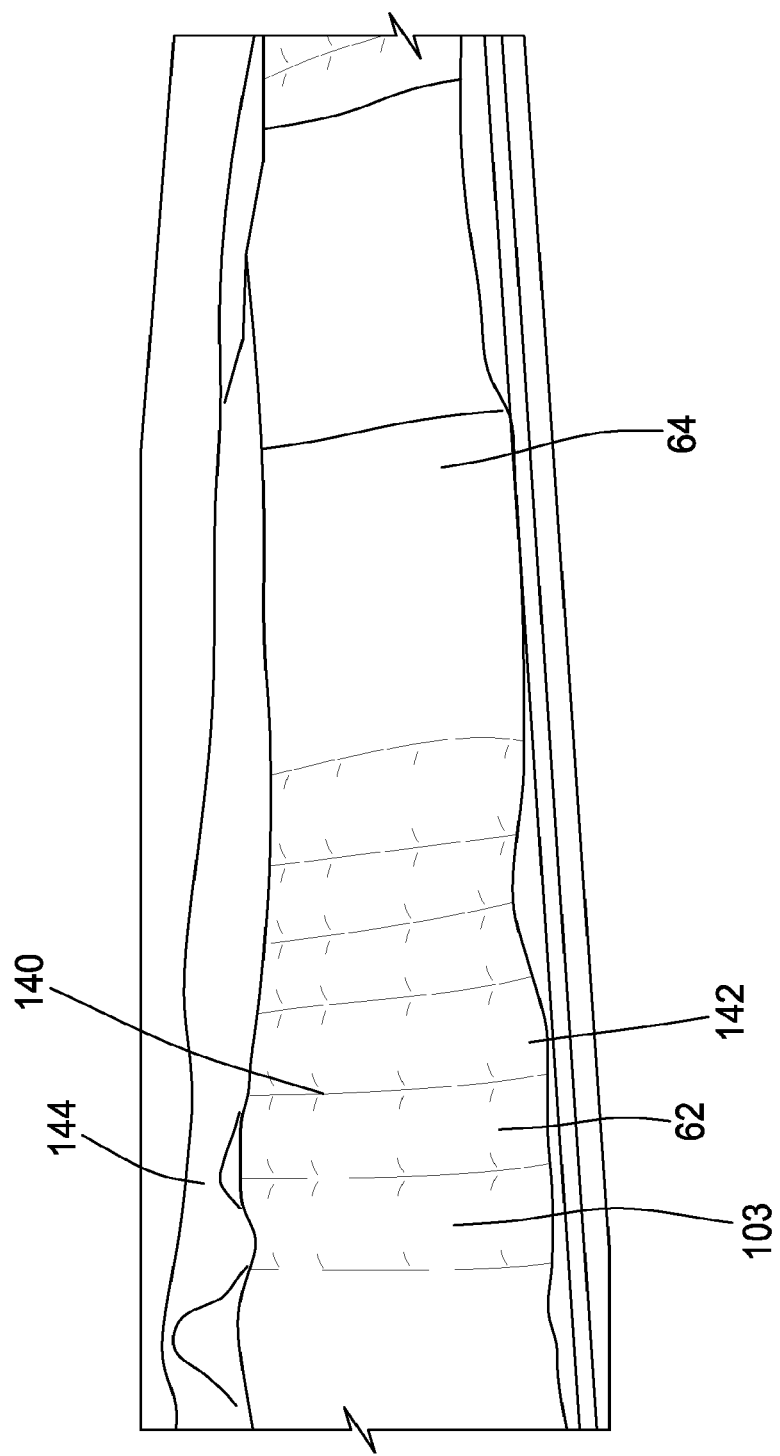
FIG. 4 is an illustration of a bridged absorbent web manufactured using the forming assembly shown in FIGS. 1 and 2.

FIG. 4 illustrates the bridged fibrous web 22 formed by the above-described apparatus 20. During the laying of the fibrous material, vertical interfaces 140 are formed in the fibrous web 22 at locations corresponding to the partitions 72. Web segments 103 are formed in the fibrous web 22 between the vertical interfaces 140. In the illustrated embodiment, the web segments 103 have a substantially rectangular shape; however, the web segments 103 may have any shape in suitable embodiments. Due to the width of the vertical interfaces 140, some fibrous material forms bridging 142 across the vertical interfaces 140, i.e., some fibrous material extends between the web segments 103. The web segments 103, vertical interfaces 140, and bridging 142 create a micro-gradient of basis weight through the bridged area 62 of the fibrous web 22, which will be discussed in more detail below.

The amount of the bridging 142 across the vertical interfaces 140 can be at least partially controlled by controlling the width of the partitions 72. The partitions 72 having a smaller width will form narrower vertical interfaces, resulting in formation of greater amounts of the bridging 142. Alternately, increasing the width of the partitions 72 will decrease the amount of the bridging 142. Once a maximum width is reached, practically all of the bridging 142 will be eliminated and a void will be formed. Therefore, preferably the partitions 72 have a width less than the maximum width. In suitable embodiments, the partitions 72 have a width less than 1 cm. The maximum width depends, at least in part, on the thickness of the fibrous web 22 that is formed on the masking plate 60. A thicker fibrous web 22 can have partitions 72 with a greater maximum width than thinner fibrous webs 22. In one suitable embodiment, the fibrous web 22 has a thickness of 6.35 mm prior to being compressed or otherwise processed.

The amount of the bridging 142 across the vertical interfaces 140 can also be at least partially controlled by the pattern height 131 of the masking plates 60. The pattern height 131 facilitates fibrous material being displaced by the partitions 72 and forming the bridging 142. Preferably, the pattern height 131 is configured to allow the bridging 142 to extend across 10-90% of at least one of the vertical interfaces 140. More preferably, the pattern height 131 is configured to allow the bridging 142 to extend across 25-75% of at least one of the vertical interfaces 140. In suitable embodiments, a pattern height 131 less than 1 cm will allow the bridging 142 to extend across 10-90% of at least one of the vertical interfaces 140 and a pattern height 131 between about 3 and about 10 mm will allow the bridging 142 to extend across 25-75% of at least one of the vertical interfaces 140.

The material forming the bridging 142 may be controlled during the formation of the fibrous web 22. For example, a majority of the superabsorbent material may be deposited close to the forming surface 24 and other particles and fibers may be deposited farther from the forming surface 24. As a result, the other particles and fibers will form substantially all of the bridging 142 across vertical interfaces 140, providing an increased strength to the bridging 142. Suitably, between about 66% and about 100% of the superabsorbent material may be deposited close to the forming surface 24. Preferably, between about 75% and about 100% of the superabsorbent material may be deposited close to the forming surface 24.

The fibrous web 22 shown in FIG. 4 was formed on a substrate 144. The substrate 144 facilitates removing the fibrous web 22 from the forming surface 24 and provides support for the fibrous web 22. However, in some embodiments, the fibrous web 22 can be formed directly on the forming surface 24 without the substrate 144. The bridging 142 across the vertical interfaces 140 provides the fibrous web 22 sufficient strength to maintain web integrity during processing without the substrate 144. In some embodiments, the fibrous web 144 can be transferred from the forming surface 24 to a substrate 144 prior to processing.

In some embodiments, the vertical interfaces 140 can define lines of weakness where a bridged absorbent structure is more flexible and/or can be easily separated. The lines of weakness can be especially beneficial when the absorbent structure is used in a personal care article, where flexibility increases the comfort for the wearer. Therefore, the bridged areas 62, and, thus, the vertical interfaces 140, can be located in portions of the absorbent structure where increased flexibility is desired. Additionally, the vertical interfaces 140 can provide beneficial fluid channeling to increase the performance of absorbent articles incorporating the absorbent structure.

The continuous areas 64 of the fibrous web 22 are free from voids and vertical interfaces 140 such that the continuous areas 64 are substantially continuous. Therefore, the continuous areas 64 have a higher basis weight than the bridged areas 62 of the fibrous web 22. In suitable embodiments, the continuous areas 64 may be in any portions of the absorbent structures. In the exemplary embodiments, the fibrous web 22 is formed and divided such that the continuous areas 64 are formed in the front area of the absorbent structures. In suitable embodiments, the fibrous web 22 can be formed and divided such that the continuous areas 64 are formed in the median area of the absorbent structures.

In suitable embodiments, the continuous area 64 covers the portion of the absorbent structure not covered by bridged areas 62. Preferably, the continuous area 64 for each formed absorbent structure covers between about 25% and about 80% of the entire area of the absorbent structure. More preferably, the continuous area 64 for each formed absorbent structure covers between about 34% and about 70% of the entire area of the absorbent structure. Most preferably, the continuous area 64 for each formed absorbent structure covers between about 40% and about 67% of the entire area of the absorbent structure.

Figure 5:
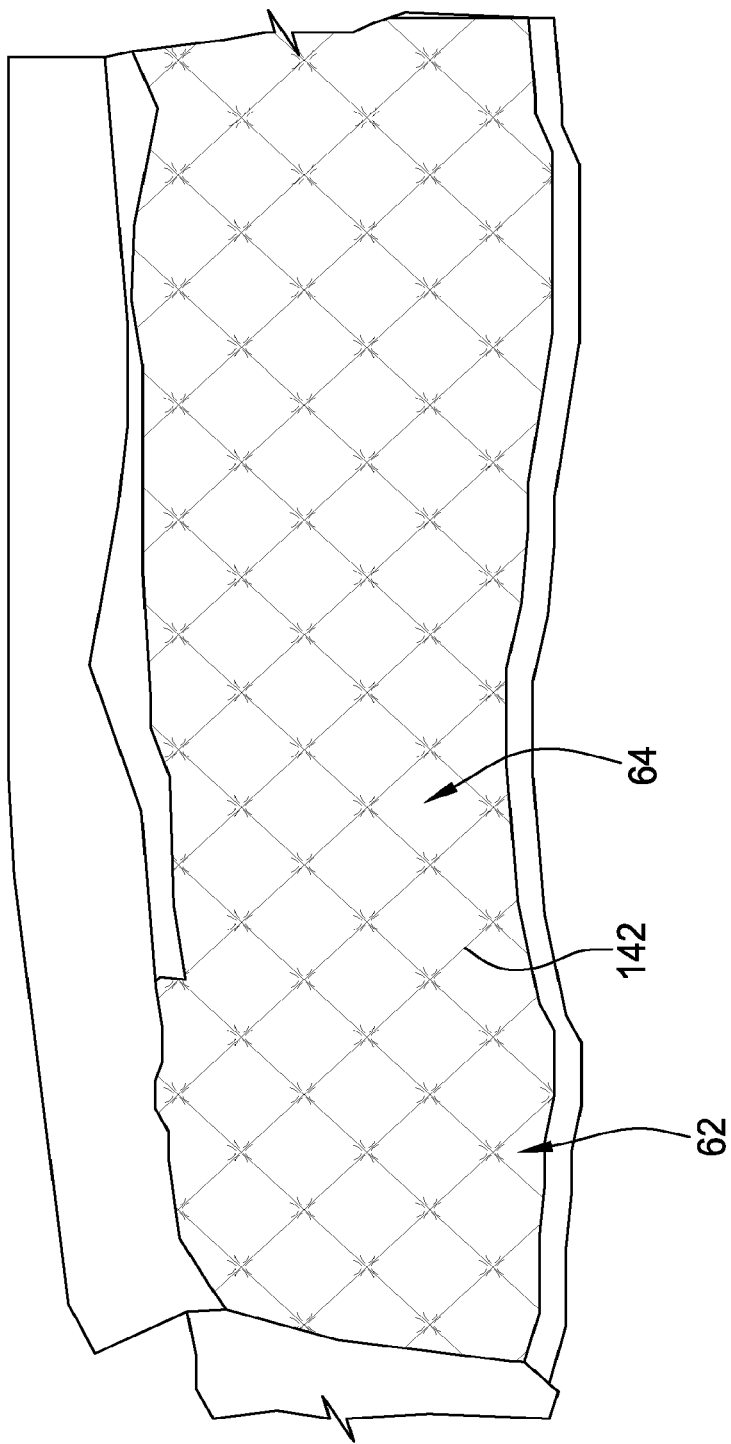
FIG. 5 is an illustration of the absorbent web of FIG. 4 after patterned debulking.
Figure 7:
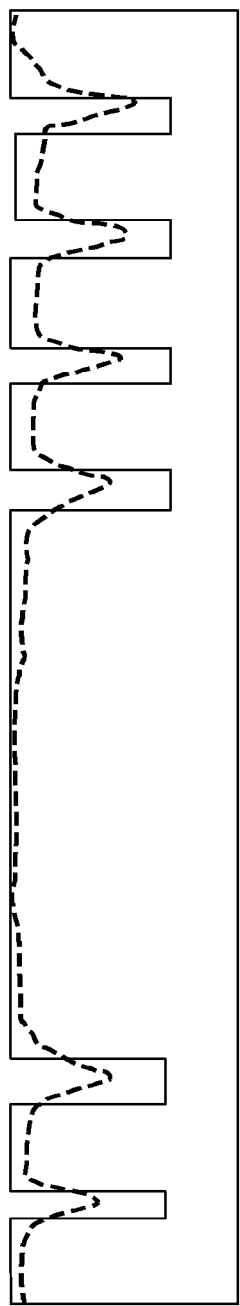
FIG. 7 is a basis weight profile through an absorbent structure.

FIG. 5 illustrates the bridged fibrous web 22 after patterned debulking. In suitable embodiments, the fibrous web 22 may be debulked in any acceptable manner and may or may not be imprinted with any suitable pattern. In the exemplary embodiment, the fibrous web 22 is imprinted with a repeating pattern of diamonds. The patterned debulking process facilitates further displacing the fibrous material from the web segments 103 into the vertical interfaces and enhancing the micro-gradient in the areas of lower basis weight, as can be seen in FIG. 7.

FIG. 6 shows a series of contour plots of absorbent structures formed using the described process. The contour plots are x-ray views illustrating the distribution of fibrous material and superabsorbent material through the absorbent structures. Each absorbent structure includes a layer of fibrous material having the bridged area 62 and the continuous area 64. Each absorbent structure has low basis weight in the bridged area 62 and high basis weight in the continuous area 64 forming the macro-gradient through the absorbent structure. In addition, the bridging 142 in the low basis weight bridged area 62 forms variations in basis weight defining the micro-gradient.

The plots show the high basis weight areas and low basis weight areas of the absorbent structures and differentiate the areas by the darkness of the shading. The differences in basis weight between the high basis weight areas and the low basis weight areas define a macro-gradient in the absorbent structure. Additionally, the low basis weight areas have a visually evident micro-gradient where the basis weight varies through the low basis weight areas. As used herein, macro-gradient means a variation of increasing and/or decreasing basis weights through substantially all of an item. As used herein, micro-gradient means a secondary variation of increasing and/or decreasing basis weight through a portion of an item.

The vertical interfaces 140, web segments 103, and the bridging 142 form variations in the basis weight through the low basis weight bridged areas 62 of the fibrous web 22, i.e., the micro-gradient. During the formation of the fibrous web 22, some fibrous material extends, or bridges, across the vertical interfaces 140 forming the bridging 142 instead of collecting in the web segments 103. Therefore, the bridging 142 lessens the amount of fibrous material in the web segments 103. Additionally, the bridging 142 provides some fibrous material in the vertical interfaces 140, which causes the vertical interfaces 140 to have a basis weight greater than zero. Therefore, the basis weight varies through the bridged areas 62 defining the micro-gradient. Additionally, fibrous material is redistributed when the fibrous web 22 is further processed, such as during the scarfing and/or debulking stages. This redistribution further enhances the bridging 142 causing a pronouncement of the micro-gradient.

FIG. 7 is a basis weight profile through an absorbent structure. The basis weight profile of the absorbent structure prior to being compressed is shown as a solid line. The basis weight profile of the absorbent structure after being compressed is shown as a dashed line. In the exemplary embodiment, the absorbent structure was compressed in a debulking process.

FIGS. 8-12 show example embodiments of masking plates 60 for use in forming fibrous webs. Each of the masking plates 60 defines an open area 100 and a partitioned area 82. In suitable embodiments, the masking plates 60 may have any number of open areas 100 and partitioned areas 81, 83 that are configured in any manner. In the illustrated embodiments, the partitioned area 82 includes a first partitioned area 81 and a second partitioned area 83.

As shown in FIGS. 8-12, the first and second partitioned areas 81, 83 each have a length 128 and a width 130. In the illustrated embodiments, the length 128 extends in the longitudinal direction and is measured between an edge 132 of the masking plate 60 and an edge 134 of the open area 100. In the illustrated embodiments, the width 130 extends in a transverse direction and is measured between maximum lateral extents 136 of the partitioned area 81, 83.

The masking plates 60, as illustrated in FIGS. 8-12, each have a cumulative pattern length. The cumulative pattern length is the summation of the perimeters of the segments 102 of each masking plate 60. Preferably, the cumulative pattern length is between about 12 mm and about 254 mm. More preferably, the cumulative pattern length is between about 63 mm and about 190 cm.

Figure 8:
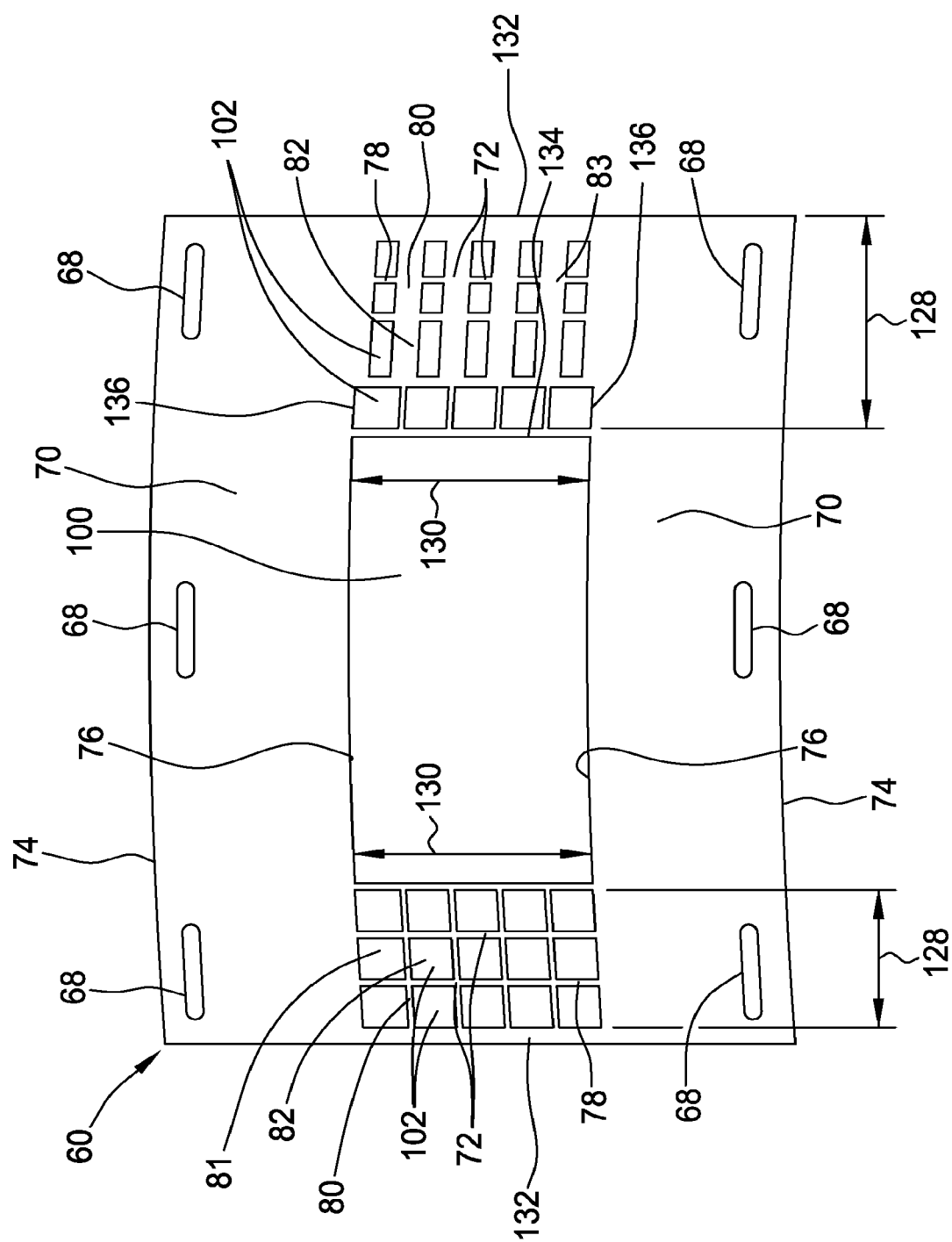
FIGS. 8-12 are embodiments of suitable masking plates having partitions for forming bridged absorbent webs.

The masking plate 60 in FIG. 8 has a substantially rectangular open area 100, a first partitioned area 81 on one side of the open area 100, and a second partitioned area 83 on the opposite side of the open area 100. In suitable embodiments, the first and second partitioned areas 82 may be identical and/or symmetric. Additionally, the partitions 72 may define segments 102 of any shape and size in suitable embodiments. For example, the partitions may define segments 102 having geometric shapes such as squares, triangles, trapezoids, and circles.

The first partitioned area 81 has a plurality of grid-like partitions 72 defining aligned, similar square segments 102. In contrast, the second partitioned area 83 has partitions 72 of different widths and lengths defining differing rectangular segments 102. Due to the differing sizes and shapes, at least some of the partitions 72 and segments 102 are offset from bordering partitions 72 and segments 102. It is believed that this offset configuration may facilitate forming a stronger fibrous web 22.

Figure 9:
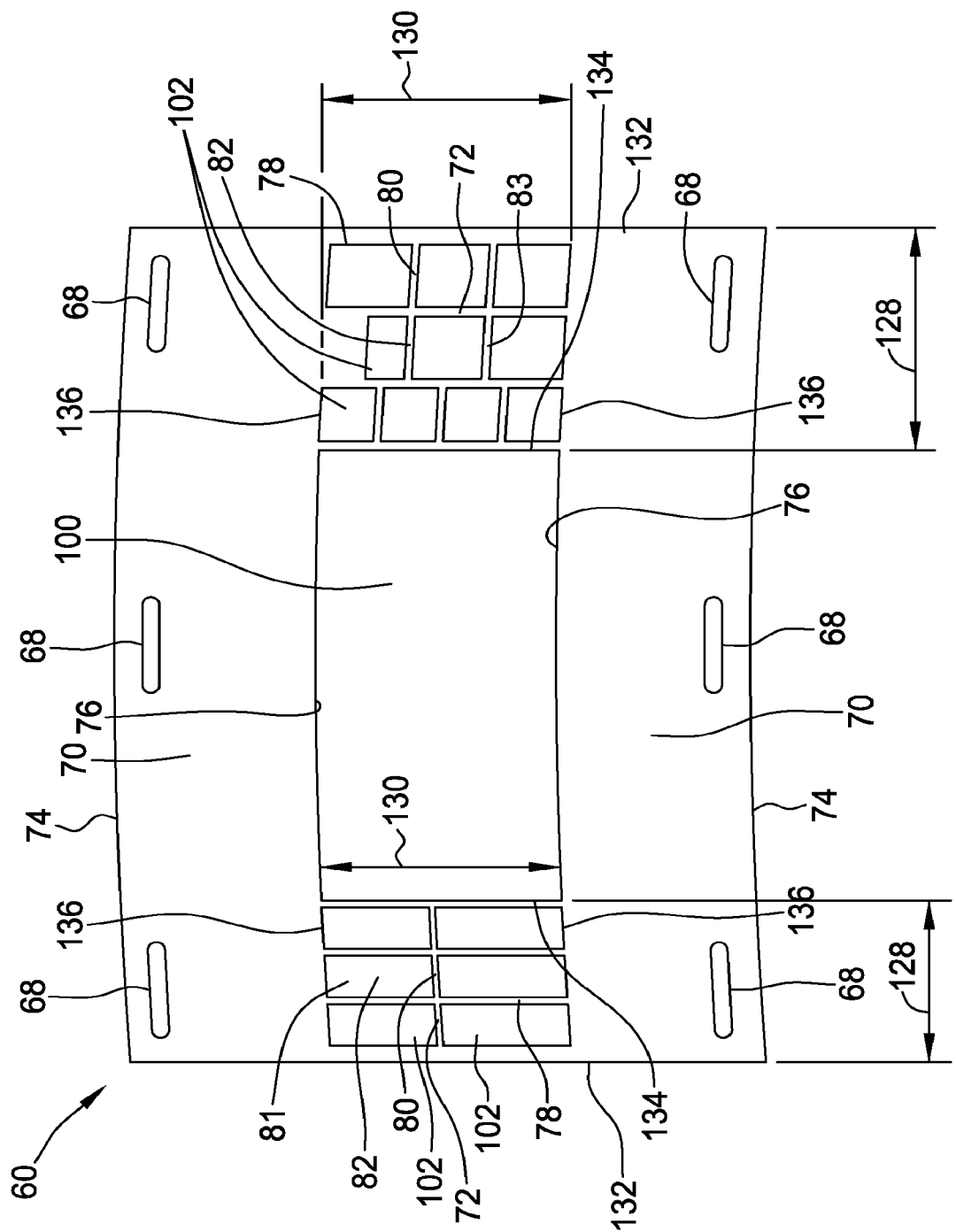

The masking plate 60 in FIG. 9 also has a substantially rectangular open area 100, a first partitioned area 81 on one side of the open area 100, and a second partitioned area 83 on the opposite side of the open area 100. The first partitioned area 81 has a plurality of grid-like partitions 72 defining aligned, similar square segments 102. In contrast, the second partitioned area 83 has partitions 72 of different widths and lengths defining differing rectangular segments 102 that are offset.

Figure 10:
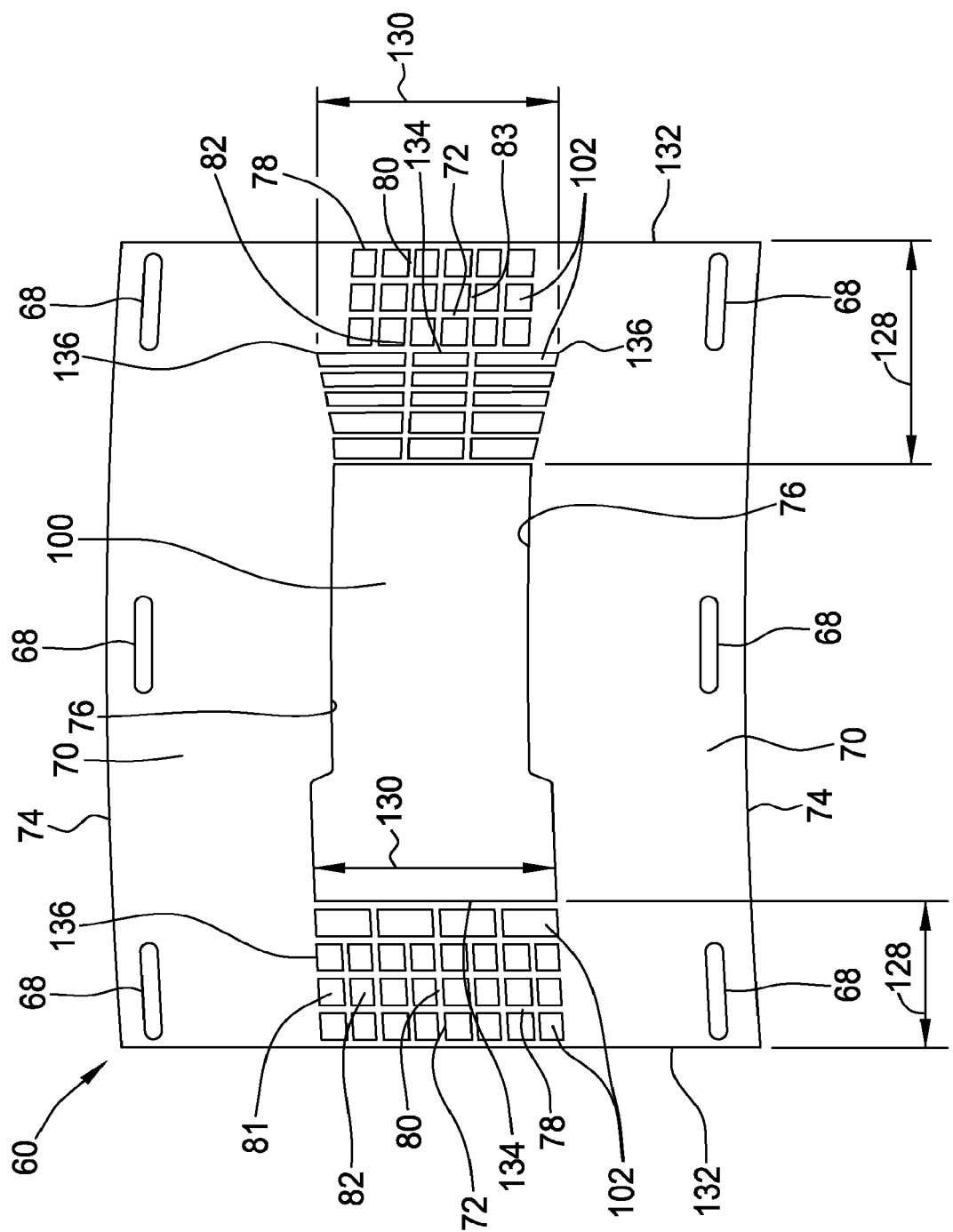

The masking plate 60 in FIG. 10 has an open area 100, a first partitioned area 81 on one side of the open area 100, and a second partitioned area 83 on the opposite side of the open area 100. The first and second partitioned areas 82, 83 have partitions 72 of different widths and lengths defining differing segments 102 that are offset. Some partitions 72 in the second partitioned area 83 are angled in relation to the edge of the masking plate 60 such that the partitions 72 define trapezoidal segments 102. Additionally, the side walls 70 define angled portions of the open area 100.

Figure 11:
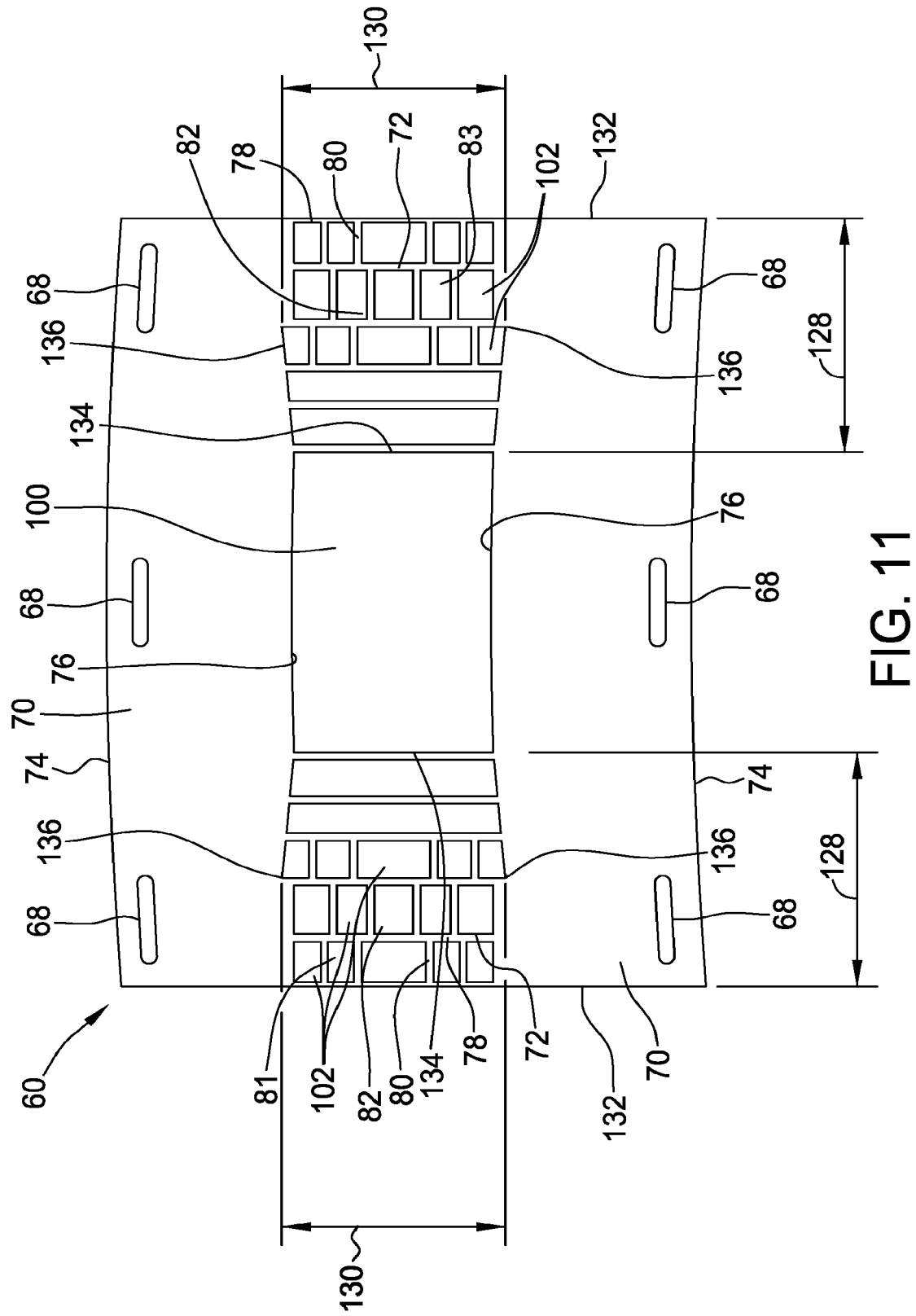

The masking plate 60 in FIG. 11 has an open area 100, a first partitioned area 81 on one side of the open area 100, and a second partitioned area 83 on the opposite side of the open area 100. The first and second partitioned areas 81, 83 are substantially symmetric to each other relative to a midline running through the open area 100. The first and second partitioned areas 81, 83 have rectangular and trapezoidal segments 102.

Figure 12:
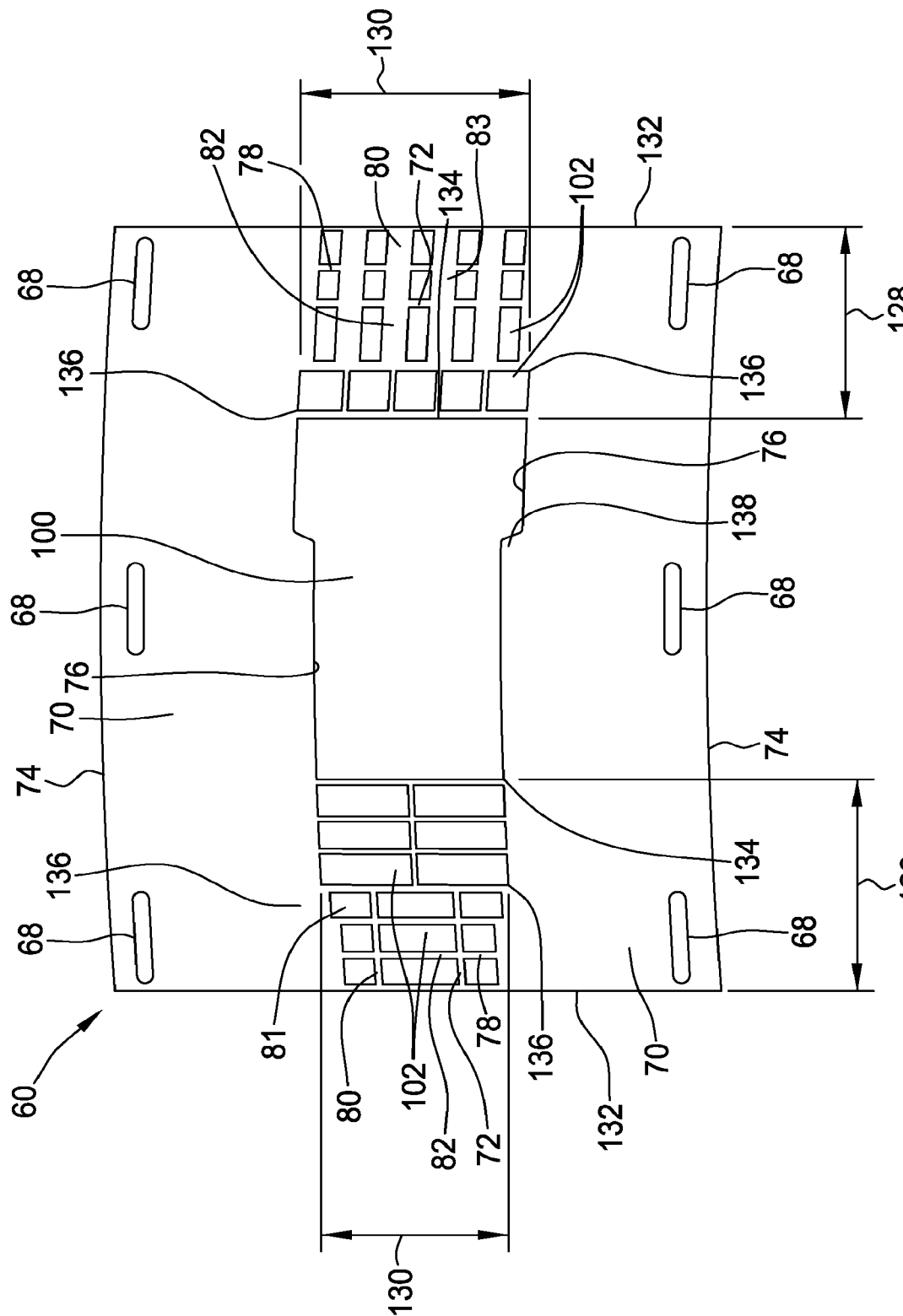

The masking plate 60 in FIG. 12 has an open area 100, a first partitioned area 81 on one side of the open area 100 and a second partitioned area 83 on the opposite side of the open area 100. The side walls 70 of the masking plate 60 each have a step 138 where the width of the open area 100 changes.

Figure 13:
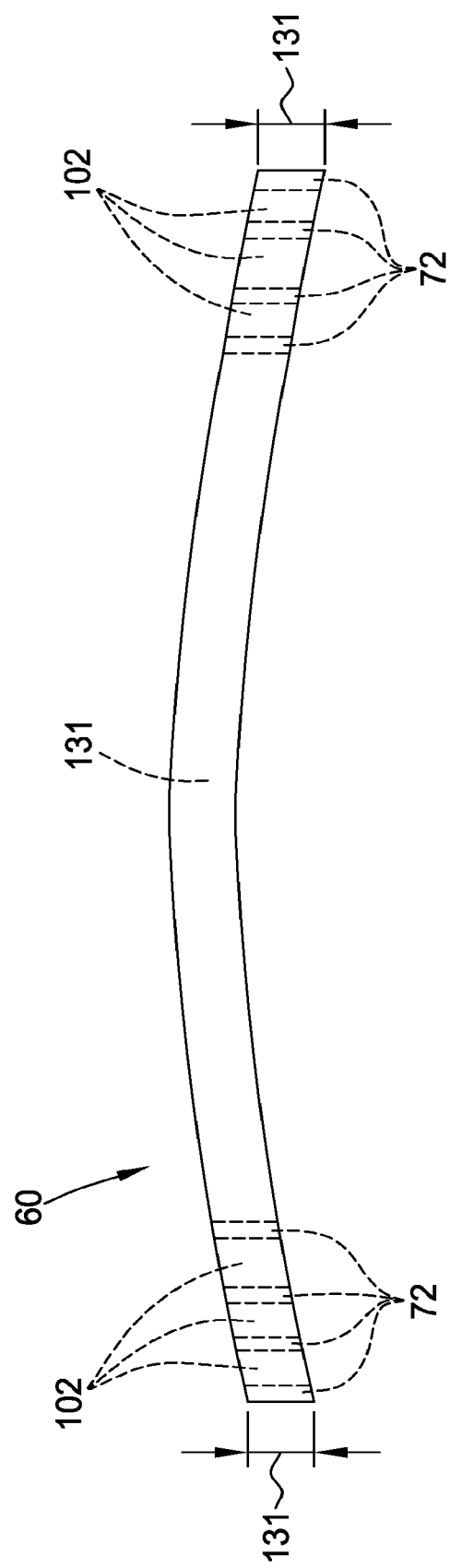
FIG. 13 is a side view of one suitable embodiment of a masking plate having partitions for forming bridged absorbent webs.

As shown in FIG. 13, each masking plate 60 has a pattern height 131. The pattern height 131 is the thickness of the masking plate 60 in the partitioned areas 82 of the masking plate 60. It is understood that the masking plates 60 can have any pattern heights 131 and the pattern heights 131 can vary or be constant throughout the partitioned areas 82. For example, in one embodiment, the masking plate 60 can have a constant pattern height 131 in the first partitioned area 81 and can have a varying pattern height 131 in the second partitioned area 83. Preferably, the pattern height 131 is less than 1 cm. More preferably, the pattern height 131 is between about 3 mm and about 10 mm.

Figure 14:
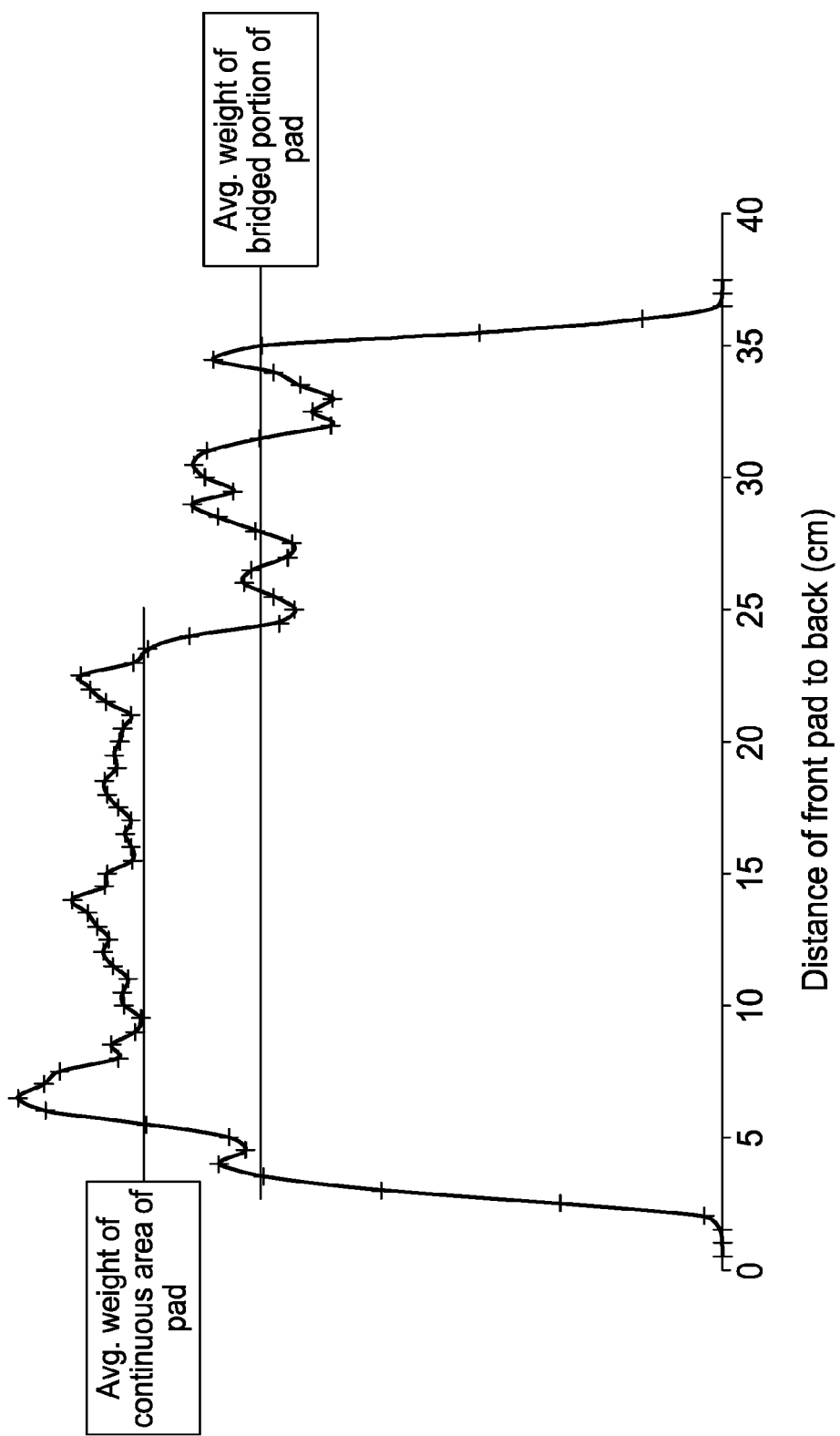
FIG. 14 is a chart showing the basis weights of an absorbent core pad compared to the distance from ends of the absorbent core pad.

FIG. 14 shows a chart of the basis weight distribution of an absorbent structure formed with another suitable embodiment of the exemplary processes. The absorbent structure has areas of higher basis weight near its median portions and areas of lower basis weight near its front and back end portions. As can be seen in the chart, the average basis weight of the continuous area 64 is higher than the average basis weight of the bridged area 62.

The data graphically illustrated in FIG. 14 was collected from analysis collected from a plurality of absorbent pad samples formed in accordance with this disclosure. The basis weight profile of the absorbent pads was measured using x-ray densitometry. Densitometry is defined as "the quantitative measurement of optical density in light-sensitive materials, such as photographic paper or photographic film, due to exposure to light." The light used was x-ray and the optical density was derived from the gray scale measure from a digital x-ray image (see FIG. 6).

The x-ray image was collected for each pad and using image analysis software, the pad image was dissected into 2.5 mm×2.5 mm sections. The program that was used had a calibration curve that converted the gray scale of all pixels within each section to mass and thus report the mass in each section.

With reference to FIG. 14, the data shows that the average mass in the front and back zones can be varied and that the lower basis weight region has a high coefficient of variance of the weight of the section suggesting a pattern variation in that zone.

FIG. 15 shows an example absorbent article including an absorbent structure manufactured with the described process. The exemplary absorbent article is in the form of a diaper illustrated in an unfastened, unfolded and laid-flat condition and indicated generally by reference number 220. The diaper 220 comprises a chassis, indicated at 221, having a generally rectangular center panel, indicated at 233, a pair of laterally opposite front side ears 234, and a pair of laterally opposite back side ears 235. For reference, arrows 223 and 225 depict the orientation of the longitudinal axis 223 and the transverse or lateral axis 225, respectively, of the diaper 220. It is contemplated that the absorbent article can have other forms without departing from some aspects of this invention (e.g., a training pant and incontinence article).

The center panel 233 of the diaper 220 is configured to contain and/or absorb exudates released by a wearer of the diaper 220. As seen in FIG. 15, the center panel 233 has a front waist region 222, a back waist region 224, and a crotch region 226 extending between and interconnecting the front and back waist regions 222, 224. The center panel 233 further includes a pair of side edges 236, a front waist edge 238, and back waist edge 239. The center panel 233 and side ears 234, 235 may comprise separate elements or be integrally formed.

The illustrated center panel 233 comprises an outer cover 240, a body-side liner 242, and an absorbent structure 244 disposed between the outer cover 240 and the body-side liner 242. In one suitable embodiment, the outer cover 240 comprises a material that is substantially liquid impermeable, and can be elastic, stretchable, or nonstretchable. The outer cover 240 can be a single layer of liquid impermeable material, but suitably comprises a multi-layered laminate structure in which at least one of the layers is liquid impermeable. For instance, the outer cover 240 can include a liquid permeable outer layer and a liquid impermeable inner layer that are joined together by a laminate adhesive, ultrasonic bonds, thermal bonds, or the like. Suitable laminate adhesives can be applied continuously or intermittently as beads, a spray, parallel swirls, or the like. The liquid permeable outer layer can be any suitable material and desirably one that provides a generally cloth-like texture. The inner layer of the outer cover 240 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 240 when a single layer, inhibits liquid exudates from wetting articles, such as bed sheets and clothing, as well as the wearer and caregiver.

The body-side liner 242 is liquid permeable and overlies the absorbent structure 244 and outer cover 240. In one suitable embodiment, a width of the body-side liner 242 is less than the width of the outer cover 240. It is understood, however, that the body-side liner 242 and the outer cover 240 can have dimensions other than those illustrated herein. For example, the body-side liner 242 and the outer cover 240 can have substantially the same dimension or the body-side liner 242 can be wider than the outer cover 240.

The body-side liner 242 suitably presents a bodyfacing surface of the diaper 220, which is compliant, soft feeling, and non-irritating to the wearer's skin. Further, the body-side liner 242 may be less hydrophilic than the absorbent structure 244, to present a relatively dry surface to the wearer, and may be sufficiently porous to be liquid permeable, permitting liquid to readily penetrate through its thickness. A suitable body-side liner 242 may be manufactured from a wide selection of web materials, such as porous foams, reticulated foams, apertured plastic films, natural fibers (i.e., wood or cotton fibers), synthetic fibers (i.e., polyester or polypropylene fibers), or a combination of natural and synthetic fibers. Various woven and nonwoven fabrics can be used for the body-side liner 242. For example, the body-side liner 242 can be composed of a meltblown or spunbonded web of polyolefin fibers. The body-side liner 242 can also be a bonded-carded web composed of natural and/or synthetic fibers. The body-side liner 242 can be composed of a substantially hydrophobic material, and the hydrophobic material can, optionally, be treated with a surfactant or otherwise processed to impart a desired level of wettability and hydrophilicity. In one suitable embodiment, for example, the body-side liner 242 can be a hydrophobic three-layer nonwoven polypropylene material known as SMS. SMS is an acronym for Spunbond, Meltblown, Spunbond, the process by which the three layers are constructed and then laminated together. One example of an SMS material is described in U.S. Pat. No. 4,041,203 to Brock et al. The body-side liner 242 is suitably employed to help isolate the wearer's skin from liquids held in the absorbent structure 244.

The absorbent structure 244 is generally compressible, conformable, non-irritating to the wearer's skin, and capable of absorbing and retaining liquids and certain body wastes, and may be manufactured in a wide variety of sizes and shapes, and from a wide variety of liquid absorbent materials commonly used in the art. The exemplary absorbent structure 244 includes a layer 243 of fibrous material having areas of high basis weight and areas of low basis weight. In suitable embodiments, a wrapsheet 251 is wrapped about at least one face of the absorbent structure 244. In the illustrated embodiment, the wrapsheet 251 suitably covers the bodyside face (i.e., that faces the wearer when the absorbent article is worn), the side edges, and a portion of the garment side face of the absorbent structure 244.

In the illustrated embodiment, a width of the absorbent structure 244 varies along its length. More specifically, the illustrated absorbent structure 244 has a width of approximately 115 millimeters in the front waist region 222 of the center panel 233 and approximately 101 millimeters in the back waist region 224 of the absorbent structure 244. The width of the absorbent structure 244 tapers inward along its length from the front waist region 222 and the back waist region 224 towards the crotch region 226 to a minimum width of the absorbent structure 244. The minimum width of the illustrated absorbent structure 244, which is the crotch region 226 of the center panel 233, is approximately 85 millimeters. It is understood that the absorbent structure 244 can have any suitable shape and size.

The absorbent structure 244 has a continuous area 245 and a bridged area 246. The continuous area 245 has a higher basis weight than the bridged area 246. Additionally, as discussed above, in the bridged area 246, the absorbent structure 244 has vertical interfaces 247 separating segments 248 and bridging 249 extending across the vertical interfaces 247. In suitable embodiments, the absorbent structure 244 may have any shape and any number of continuous and bridged areas 245, 246.

The center panel 233 can also incorporate other materials designed primarily to receive, temporarily store, and/or transport liquid along the mutually facing surface with absorbent structure 244, thereby maximizing the absorbent capacity of the absorbent assembly. One suitable material is referred to as a surge management layer (not shown) and may be located between the absorbent assembly and the body-side liner 242. The surge management layer helps to decelerate and diffuse surges or gushes of liquid that may be rapidly introduced into the absorbent structure 244. The surge management layer can rapidly accept and temporarily hold the liquid prior to releasing the liquid into the storage or retention portions of the absorbent structure 244. Examples of suitable surge management layers are described in U.S. Pat. Nos. 5,486,166 and 5,490,846. Other suitable surge management materials are described in U.S. Pat. No. 5,820,973.

As seen in FIG. 15, the front and back side ears 234, 235 are disposed on laterally opposite sides of the center panel 233 in longitudinally spaced relationship with each other. In the illustrated embodiment, the back side ears 235 are permanently bonded along seams to the center panel 233 in the respective back waist region 224. More specifically, each of the back side ears 235 are sandwiched between the outer cover 240 and the body-side liner 242 permanently bonded to both the outer cover and the body-side liner 242. The front side ears 234 are integrally formed with the center panel 233. The front side ears 234 extend transversely outward beyond the side edges 236 of the center panel 233 in the front waist region 222, and the back side ears 235 extend transversely outward beyond the side edges 236 of the central panel 233 in the back waist region 224.

In suitable embodiments, the front and back side ears 234, 235 may be bonded to the center panel 233 using any attachment means known to those skilled in the art such as adhesive, thermal or ultrasonic bonding. In the illustrated embodiment, for example, the back side ears 235 are adhesively bonded to both the outer cover 240 and the body-side liner 242. As mentioned above, the front and back side ears 234, 235 can be formed as an integral portion of a component of the center panel 233. For example, the front and back side ears 234, 235 can comprise a generally wider portion of the outer cover 240 and/or the body-side liner 242.

In one suitable embodiment, the front and back side ears 234, 235 comprise an elastic material capable of stretching in a direction generally parallel to the transverse axis 225 of the diaper 220. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al. Alternatively, the side panel material may comprise other woven or nonwoven materials, such as those described above as being suitable for the outer cover 240 or body-side liner 242, mechanically pre-strained composites, or stretchable but inelastic materials.

The illustrated diaper 220 includes a fastening system 280 for refastenably securing the diaper 220 about a waist of the wearer. The illustrated fastening system 280 includes first fastening components 284 adapted for refastenable engagement to corresponding second fastening components 282. In the illustrated embodiment, the first fastening components 284 comprise a plurality of projecting engaging elements. The engaging elements of the first fastening components 284 are adapted to repeatedly engage and disengage engaging elements of the second fastening components 282.

The fastening components 284, 282 can comprise separate elements bonded to the side ears 234, 235, or they may be integrally formed with the side ears 234, 235. In the illustrated embodiment, for example, the first fastening components 284 are formed separate from the front side ears 234 and bonded thereto. The second fastening components 282, on the other hand, are integrally formed with the back side ears 235. The first fastening components 284 can be bonded to the respective front side ears 234 by any means known to those skilled in the art such as adhesive bonds, ultrasonic bonds or thermal bonds.

The fastening components 284, 282 can comprise any refastenable fasteners suitable for absorbent articles, such as adhesive fasteners, cohesive fasteners, mechanical fasteners, or the like. In the illustrated embodiment, the fastening components 284, 282 comprise mechanical fastening elements. Suitable mechanical fastening elements can be provided by interlocking geometric shaped materials, such as hooks, loops, bulbs, mushrooms, arrowheads, balls on stems, male and female mating components, buckles, snaps, or the like.

Figure 16:
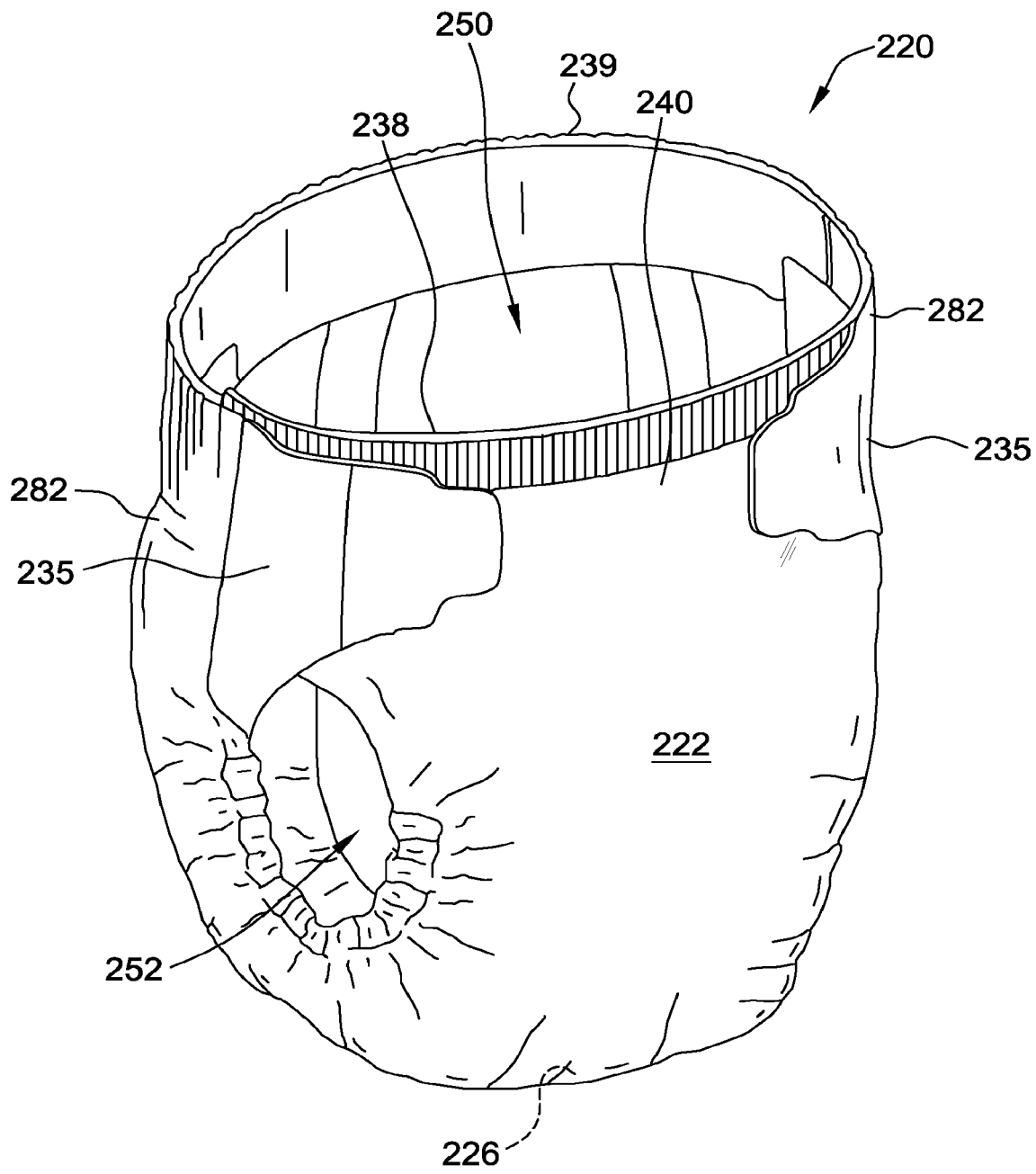
FIG. 16 is a perspective view of the absorbent article of FIG. 15, the absorbent article being illustrated in a use configuration.

In a ready-to-wear, three dimensional configuration of the diaper 220, which is illustrated in FIG. 16, the front and back side ears 234, 235 are secured together to define a three-dimensional wear configuration having a waist opening 250 and a pair of leg openings 252. The front waist region 222 comprises the portion of the diaper which, when worn, is positioned on the front of the wearer while the back waist region 224 comprises the portion of the diaper which, when worn, is positioned on the back of the wearer. The crotch region 226 of the diaper 220 comprises the portion of the diaper which, when worn, is positioned between the legs of the wearer and covers the lower torso of the wearer. The front and back side ears 234, 235 define the portions of the diaper 220 which, when worn, are positioned on the hips of the wearer. The waist edges 238, 239 of the diaper chassis 221 are configured to encircle the waist of the wearer when worn and together define the waist opening 250.

As seen in FIG. 16, in the ready-to-wear, three dimensional configuration of the diaper 220, the back side ears 235 overlap the front side ears 234 when the first fastening component 284 is engaged with the second fastening component 282. It is understood, however, that the diaper 220 may instead be configured so that the front side ears 234 overlap the back side ears 235.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "top", "bottom", "above", "below" and variations of these terms is made for convenience, and does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A method of forming an absorbent structure for use in an absorbent article, the method comprising:
    moving a forming surface having at least one masking plate mounted thereon in a machine direction;
    drawing air through the forming surface and the masking plate mounted on the forming surface, the masking plate having partitions, each partition having a width that is less than 1 cm for at least partially blocking air being drawn through the forming surface;
    depositing fibrous material on the forming surface to form a fibrous web, the partitions of the masking plate displacing the fibrous material into a plurality of segments separated by vertical interfaces, the vertical interfaces corresponding to the locations of the partitions wherein at least one segment of the plurality of segments has an area between 10 mm$^2$ and 2,500 mm$^2$; and
    removing the fibrous web from the forming surface.

2. The method set forth in claim 1 further comprising displacing fibrous material to at least partially bridge the vertical interfaces.

3. The method set forth in claim 1 wherein the masking plate includes at least one continuous open area that is substantially free of obstructions, allowing the deposition of web material directly on the forming surface.

4. The method set forth in claim 3 further comprising forming at least one void in the fibrous web.

5. The method set forth in claim 3 wherein the open area in the masking plate has a continuous area between about 10 cm² and about 750 cm².

6. The method set forth in claim 5 wherein the open area in the masking plate has a continuous area between about 200 cm² and about 500 cm².

7. The method set forth in claim 1 further comprising scarfing fibrous material from the fibrous web.

8. The method set forth in claim 7 further comprising redistributing some of the fibers of the fibrous web.

9. The method set forth in claim 1 further comprising passing the fibrous web between a pair of debulking rolls.

10. The method set forth in claim 1 further comprising folding the fibrous web about at least one of the vertical interfaces.

11. A method of forming an absorbent structure for use in an absorbent article, the method comprising:
    moving a forming surface having at least one masking plate mounted thereon in a machine direction;
    drawing air through the forming surface and the masking plate mounted on the forming surface, the masking plate having a partitioned area including partitions, each partition having a width that is less than 1 cm for at least partially blocking air being drawn through the forming surface;
    depositing fibrous material on the forming surface to form a fibrous web having a continuous area and a bridged area, the bridged area having a reduced basis weight compared to the continuous area and corresponding to the partitioned area of the masking plate, the partitions of the masking plate displacing the fibrous material into a plurality of segments separated by vertical interfaces, the vertical interfaces corresponding to the locations of the partitions wherein at least one segment of the plurality of segments has an area between 10 mm² and 2,500 mm²; and
    removing the fibrous web from the forming surface.

12. The method set forth in claim 11 further comprising displacing fibrous material to at least partially bridge the vertical interfaces.

13. The method set forth in claim 11 wherein the masking plate includes at least one continuous open area that is substantially free of obstructions, allowing the deposition of web material directly on the forming surface.

14. The method set forth in claim 11 scarfing fibrous material from the fibrous web.

15. The method set forth in claim 11 further comprising passing the fibrous web between a pair of debulking rolls.

16. The method set forth in claim 11 further comprising folding the fibrous web about at least one of the vertical interfaces.

17. A method of forming an absorbent structure for use in an absorbent article, the method comprising:
    moving a forming surface having at least one masking plate mounted thereon in a machine direction;
    drawing air through the forming surface and the masking plate mounted on the forming surface, the masking plate having partitions, each partition having a width that is less than 1 cm for at least partially blocking air being drawn through the forming surface;
    depositing fibrous material on the forming surface to form a fibrous web, the partitions of the masking plate displacing the fibrous material into a plurality of segments separated by vertical interfaces, the vertical interfaces corresponding to the locations of the partitions, the vertical interfaces have a vertical depth and extend longitudinally and laterally separating segments within a bridged area of the fibrous web; and
    removing the fibrous web from the forming surface.

18. The method set forth in claim 17 further comprising displacing fibrous material to at least partially bridge the vertical interfaces.

19. The method set forth in claim 17 wherein the masking plate includes at least one continuous open area that is substantially free of obstructions, allowing the deposition of web material directly on the forming surface.

20. The method set forth in claim 17 further comprising scarfing fibrous material from the fibrous web.

* * * * *